US009944957B2

(12) United States Patent
Ma et al.

(10) Patent No.: US 9,944,957 B2
(45) Date of Patent: Apr. 17, 2018

(54) **RECOMBINANT *ESCHERICHIA COLI* FOR PRODUCING D-LACTATE AND USE THEREOF**

(71) Applicant: Tianjin Institute of Industrial Biotechnology, Chinese Academy of Sciences, Tianjin (CN)

(72) Inventors: Yanhe Ma, Tianjin (CN); Xueli Zhang, Tianjin (CN); Hongtao Xu, Tianjin (CN); Xinna Zhu, Tianjin (CN); Pingping Liu, Tianjin (CN); Jinlei Tang, Tianjin (CN)

(73) Assignee: TIANJIN INSTITUTE OF INDUSTRIAL BIOTECHNOLOGY, CHINESE ACADEMY OF SCIENCES, Tianjin (CN)

( * ) Notice: Subject to any disclaimer, the term of this patent is extended or adjusted under 35 U.S.C. 154(b) by 180 days.

(21) Appl. No.: 14/904,179

(22) PCT Filed: Jul. 9, 2014

(86) PCT No.: PCT/CN2014/081878
§ 371 (c)(1),
(2) Date: Jan. 11, 2016

(87) PCT Pub. No.: WO2015/003629
PCT Pub. Date: Jan. 15, 2015

(65) Prior Publication Data

US 2016/0145653 A1 May 26, 2016

(30) Foreign Application Priority Data

Jul. 12, 2013 (CN) .......................... 2013 1 0293659

(51) Int. Cl.

| | |
|---|---|
| ***C12P 7/56*** | (2006.01) |
| ***C12N 9/04*** | (2006.01) |
| ***C12N 15/52*** | (2006.01) |
| ***C12N 1/20*** | (2006.01) |
| ***C12N 15/70*** | (2006.01) |

(52) U.S. Cl.
CPC .................. *C12P 7/56* (2013.01); *C12N 1/20* (2013.01); *C12N 9/0006* (2013.01); *C12N 15/52* (2013.01); *C12N 15/70* (2013.01); *C12Y 101/01028* (2013.01)

(58) Field of Classification Search
None
See application file for complete search history.

(56) References Cited

FOREIGN PATENT DOCUMENTS

CN 101988079 A 3/2011

OTHER PUBLICATIONS

Zhou et al., "Genetically switched D-lactate production in *Escherichia coli*", Metabolic Engineering 14: 560-568 (2012). (Year: 2012).*

International Search Report from PCT/CN2014/081878 dated Oct. 15, 2014.

Written Opinion from PCT/CN2014/081878 dated Oct. 15, 2014.

Grabar et al., "Methylglyoxal Bypass Identified as Source of Chiral Contamination in L(+) and D(−)-Lactate Fermentations by Recombinant *Escherichia coli*" Biotechnol Lett, vol. 28, pp. 1527-1535, Jul. 26, 2006.

Zhang et al., "Isolation of High Osmotic-Tolerant Mutants of *Escherichia coli* for Succinic Acid Production by Metabolic Evolution" Chinese Journal of Biotechnology, vol. 28, No. 11, pp. 1337-1345, Nov. 25, 2012.

Zhou et al., "Fermentation of 10% (W/V) Sugar to D(−)-Lactate by Engineered *Escherichia coli* B" Biotechnol Lett, vol. 27, pp. 1891-1896, Dec. 31, 2005.

Zhou et al., "Fermentation of 12% (W/V) Glucose to 1.2M Lactate by *Escherichia coli* Strain S2194 Using Mineral Salts Medium", Biotechnol Lett, vol. 28, pp. 663-670, Dec. 31, 2006.

* cited by examiner

*Primary Examiner* — Anand U Desai
(74) *Attorney, Agent, or Firm* — Swanson & Bratschun, L.L.C.

(57) ABSTRACT

Provided is recombinant *Escherichia coli* comprising a mutated ldhA gene. Disclosed are use of the recombinant *Escherichia coli* in the preparation of D-lactate, and method of preparing D-lactate by employing the recombinant *Escherichia coli*. In the method of preparing D-lactate, fermentation can be conducted at a high temperature (42-50° C.), and aqueous ammonia or sodium hydroxide can be used as a neutralizer during the fermentation.

12 Claims, 10 Drawing Sheets

RECOMBINANT *ESCHERICHIA COLI* FOR PRODUCING D-LACTATE AND USE THEREOF

RELATED APPLICATIONS

This application is a 35 U.S.C. § 371 national phase application of PCT/CN2014/081878 (WO 2015/003629) filed on Jul. 9, 2014, entitled "RECOMBINANT *ESCHERICHIA COLI* FOR PRODUCING D-LACTATE AND USE THEREOF", which application claims the benefit of Chinese Application No. 201310293659.6, filed Jul. 12, 2013, which is incorporated herein by reference in its entirety.

FIELD OF THE INVENTION

The invention relates to the field of producing D-lactate by *E. coli* fermentation. Specifically, the invention provides an engineered recombinant *E. coli* for producing D-lactate. The invention also relates to use of the engineered recombinant *E. coli* for producing D-lactate, and a method of using the engineered recombinant *E. coli* for producing D-lactate.

Incorporated by reference herein in its entirety is the Sequence Listing entitled "Sequence listing.txt", created Jan. 4, 2016, size of 12 kilobytes.

BACKGROUND OF THE INVENTION

D-lactate is a chiral small molecule, and is the precursor for synthesis of a variety of chiral compounds, which is widely used in medicines, pesticides and chemical industries. D-polylactic acid, synthesized by using D-lactate as starting material, is bio-degradable, and is an ideal environment-friendly polymer material: it can replace materials like polyethylene, polypropylene and polystyrene to produce novel environment-friendly package material; it can replace traditional medical materials like silicone rubber and silicone oil to produce bone fixations and medical surgical sutures etc.; it can be used in textile industry, to produce comfortable, smooth, and glossy underwear. D-lactate can be used as starting material to synthesize lactate esters, which can be used in the production of spices, resin coatings, adhesives, and printing inks; it can be used to produce excellent herbicides: Puma Super, Whip Super (Hoechst, Germany), DuplosanR (BASF, Germany).

The preparation methods of D-lactate mainly include chiral resolution, enzyme conversion and fermentation. Since chiral resolution and enzyme conversion have problems like environmental pollution and high costs, currently the large-scale production of D-lactate are mostly based on microbial fermentations. The production of D-lactate through microbial fermentation becomes the primary method for producing D-lactate, due to its low cost and high safety of the product. The production of D-lactate with high optical purity is the major limitation for microbial fermentation.

Currently there are mainly two classes of strains used for lactate fermentation. The first is natural lactate-producing bacteria (mainly *Lactobacillus*), which are important commercial strains since they have good acid resistance and can produce D-lactate with high optical purity after genetic modifications (Demirici et al. 1992, J Indust Microbiol Biotechnol 11:23-28; Okano K et al 2009, Appl Environ Microbiol 75:462-467). The drawbacks of such producing bacteria is that they need complex medium during the fermentation, and cannot utilize pentose, which increase the production costs and the downstream isolation/purification costs. For such bacteria, generally calcium hydroxide or calcium carbonate is used as neutralizer for controlling fermentative pH, and the final fermentation product is calcium lactate. However, the separation of calcium lactate generally requires addition of sulfuric acid, and produces large amounts of calcium sulfate waste which is hard to handle. More importantly, D-lactate produced by such bacteria normally has a chiral purity lower than 98%, which is not qualified for the production of polylactic acid.

The other class is metabolically engineered bacteria, including *Saccharomyces, Bacillus, Kluyveromyces*, and *Escherichia*. These engineered bacterial stains are all improved in some aspects regarding the lactate production, such as expanding substrate-utilizing range, reducing the nutritional needs, or eliminating the need for plasmids or antibiotics (Bianchi et al. 2001, Appl Environ Microbiol 67:5621-5625; Grabar et al. 2006, Biotechnol Lett 28:1527-153; Stewart et al. 2013, Yeast 30:81-91). In microbial fermentation, *E. coli* is extensively investigated to obtain high-yielding strain due to its advantages, such as clear genetic background, easy to operate, easy to regulate, easy to culture, fast growth, capable of utilizing various carbon sources and being cultured in minimal mineral salt medium. Under anaerobic conditions, *E. coli* generally consumes saccharides or derivatives thereof, and produces formate, acetate, lactate, succinate, ethanol etc. during fermentation. The yield of wild-type *E. coli* of producing lactate is generally very low. Studies in recent years indicate that, genetic modifications to metabolic pathways of *E. coli* can obtain lactate high-yielding strains. Currently modification of *E. coli* to produce high optical purity D-lactate has become the research focus.

Zhou et al. obtained recombinant *E. coli* strain SZ63 by deleting genes encoding the pyruvate formate lyase (pflB), fumarate reductase (frdABCD), alcohol dehydrogenase (adhE) and acetate kinase (ackA) in *E. coli* W3110 (Zhou et al. 2003, Applied Environ Microbiol 69:399-407). This strain SZ63 can produce 48 g/L D-lactate in mineral salts mediums containing 5% glucose after fermentation for 168 hours, wherein the D-lactate yield was nearly 2 mol/mol and the chiral purity reached 99%. Zhou et al. used the same strategy to construct recombinant strain SZ186 in *E. coli* B strain, and obtain strain SZ194 by metabolic evolution. After fermented in mineral salts mediums containing 12% glucose for 72 hours, SZ194 produced 111 g/L D-lactate with a yield of nearly 2 mol/mol and the chiral purity of 95% (Zhou et al. 2005, Biotechnol lett 27:1891-1896; Zhou et al. 2006, Biotechnol Lett 28:663-670).

Grabar et al. (Grabar et al. 2006, Biotechnol Lett 28:1527-1535) further modified the strain SZ194, by deleting methylglyoxal synthase gene mgsA to obtain recombinant strain TG112, and further to obtain strain TG114 by metabolic evolution. This strain TG114 produced 118 g/L D-lactate after fermented in mineral salts mediums containing 12% glucose for 48 hours, with the optical purity of 99.9% and a yield of glucose of 0.98 g/g.

The above engineered *E. coli* all used potassium hydroxide as neutralizer. Potassium hydroxide costs more in industrial production, while ammonia and sodium hydroxide cost much less. Therefore, it is desired to produce *E. coli* strains that can use ammonia or sodium hydroxide as neutralizer to adjust pH during the fermentation.

In order to improve the D-lactate titer and/or yield of *E. coli*, it is desired to further modify the metabolic pathways of *E. coli*. Besides, to reduce the possibility of bacterial contamination in industrial production, more improvements were needed to optimize the *E. coli* physiological properties and the temperature for D-lactate fermentation needed to be increased.

SUMMARY OF THE INVENTION

In one aspect, the invention provides a recombinant *E. coli* for producing D-lactate.

In one embodiment, the invention provides a recombinant *E. coli* comprising a mutated ldhA gene, wherein the polypeptide encoded by the mutated ldhA gene comprises a modification at the position corresponding to position R282 in the amino acid sequence shown in SEQ ID No.: 1, and the corresponding position is determined by sequence alignment with SEQ ID No.: 1. In a preferred embodiment, in said *E. coli*, the expression of said mutated ldhA gene is enhanced, and/or the activity of the protein encoded by said mutated ldhA gene is enhanced. In one embodiment, the *E. coli* of the invention further comprises the modifications of inhibited expression of pflB gene, and/or inhibited activity of the protein encoded by pflB gene; inhibited expression of frdABCD gene cluster, and/or inhibited activity of the protein(s) encoded by frdABCD gene cluster.

In one embodiment, the invention provides a recombinant *E. coli* comprising a mutated ldhA gene, wherein the polypeptide encoded by the mutated ldhA gene comprises a modification at the position corresponding to position R282 in the amino acid sequence shown in SEQ ID No.: 1, wherein the modification at the position corresponding to R282 is the replacement of R with C, and the corresponding position is determined by sequence alignment with SEQ ID No.: 1.

In one embodiment, the invention provides a recombinant *E. coli* comprising a mutated ldhA gene, wherein said mutated ldhA gene comprises a modification at the position corresponding to position C844 of the nucleotide sequence shown in SEQ ID No.: 2, and the corresponding position is determined by sequence alignment with SEQ ID No.: 2. In one preferred embodiment, in said *E. coli*, the expression of the mutated ldhA gene is enhanced, and/or the activity of the protein encoded by said mutated ldhA gene is enhanced.

In one embodiment, the invention provides a recombinant *E. coli* comprising a mutated ldhA gene, wherein said mutated ldhA gene comprises a modification at the position corresponding to position C844 of the nucleotide sequence shown in SEQ ID No.: 2, and wherein the modification is the replacement of C with T, and the corresponding position is determined by sequence alignment with SEQ ID No.: 2.

In another embodiment, the *E. coli* of the invention further comprises the modifications of inhibited expression of mgsA gene, and/or inhibited activity of the protein encoded by mgsA gene.

In one embodiment, the invention provides a recombinant *E. coli* comprising a mutated ldhA gene, wherein said mutated ldhA gene is located in a plasmid or a chromosome.

In second aspect, the invention provides a method for producing D-lactate, comprising the step of culturing the *E. coli* of the invention.

In third aspect, the invention relates to use of the *E. coli* of the invention in the production of D-lactate.

BRIEF DESCRIPTION OF FIGURES

FIG. 2A is standard D-lactate, FIG. 2B is standard L-lactate, FIG. 2C is a mixture of lactate (the optical purity of D-lactate is 99.5%), FIG. 2D is Dlac-002, FIG. 2E is Dlac-004, FIG. 2F is Dlac-006.

FIG. 5: production of D-lactate by Dlac-012 in a 5 L fermentor.

FIG. 6.

FIG. 9: the production of D-lactate by Dlac-206 in a 500 mL fermentor. The fermentation temperature is 42 degree.

DETAILED DESCRIPTION OF THE INVENTION

Unless otherwise indicated, all technical and scientific terms have the common meanings known in the art. All the patents, patent applications, publications, sequences, and other published material are incorporated herein as references, unless otherwise indicated.

In one aspect, the invention provides a recombinant *E. coli* containing a mutated ldhA gene.

As used herein, the terms "Engineered recombinant *E. coli*", "Engineered *E. coli*" and "Recombinant *E. coli*" can be used interchangeably, and all refer to modified *E. coli*, wherein the modification can be, e.g., enhanced gene expression, inhibited gene expression, introduction of a new gene, introduction of a mutated gene, or mutation to a gene; wherein the common techniques in the art can be used to achieve the enhanced gene expression or inhibited gene expression, such as gene deletion, changing gene copy number, introduction of a plasmid, changing gene promoter (e.g. using a strong or weak promoter) etc.

In one embodiment, the invention provides a recombinant *E. coli* comprising a mutated ldhA gene, wherein the polypeptide encoded by the mutated ldhA gene comprises a modification at the position corresponding to position R282 in the amino acid sequence shown in SEQ ID No.: 1, and the corresponding position is determined by sequence alignment with SEQ ID No.: 1. In one preferred embodiment, in said *E. coli*, the expression of said mutated ldhA gene is enhanced, and/or the activity of the protein encoded by said mutated ldhA gene is enhanced.

As used herein, the term "mutation" has the common meaning known in the art, and refers to insertion, addition, deletion, or replacement of one or more nucleotides in a nucleotide sequence, or refers to insertion, addition, deletion, or replacement of one or more amino acids in a polypeptide sequence.

In one embodiment, the invention provides a recombinant *E. coli* comprising a mutated ldhA gene, wherein the polypeptide encoded by the mutated ldhA gene comprises a modification at the position corresponding to position R282 in the amino acid sequence shown in SEQ ID No.: 1, wherein the modification at the position corresponding to R282 is the replacement of R with C, and the corresponding position is determined by sequence alignment with SEQ ID No.: 1.

Figure 6A:
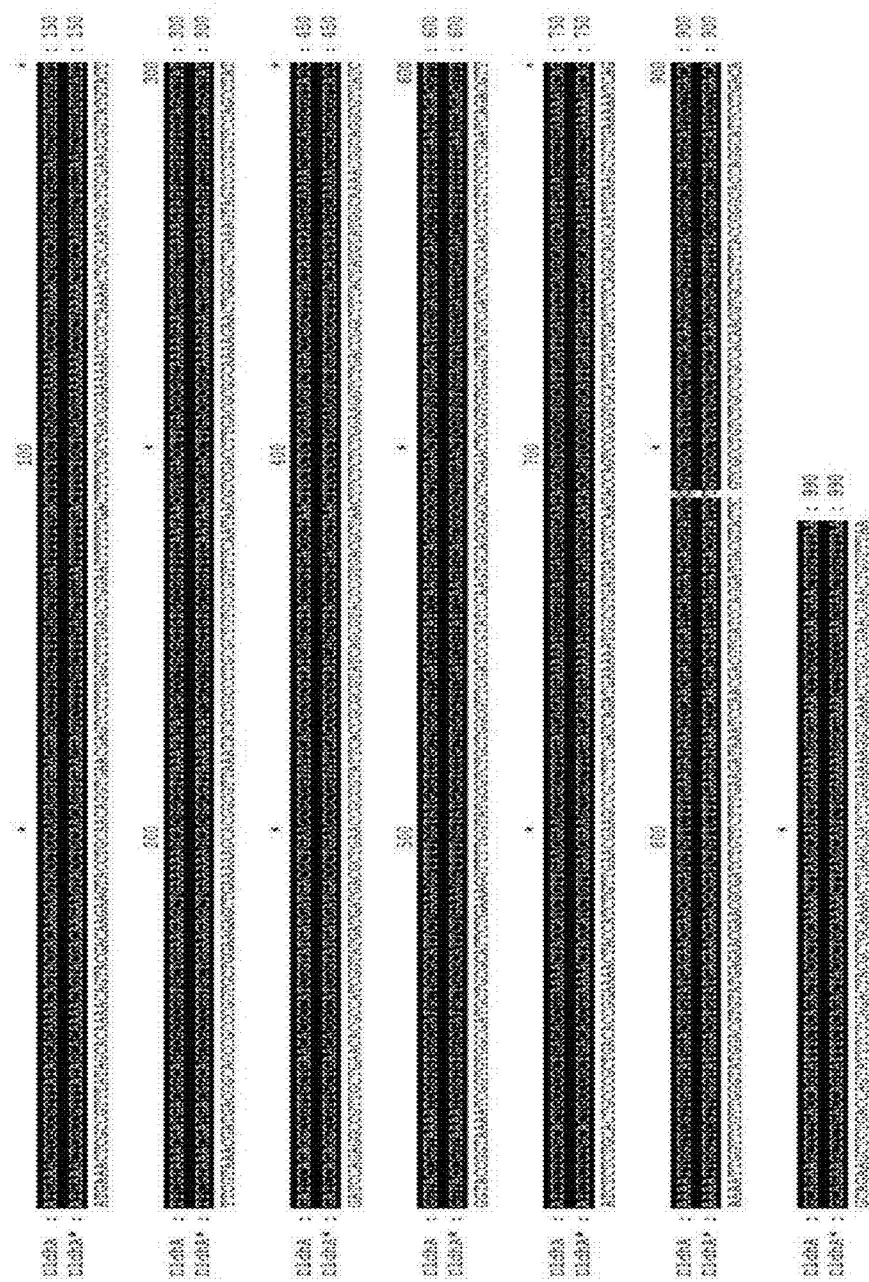
FIG. 6A shows the nucleotide sequence alignment of wild-type ldhA gene and the mutated ldhA gene (ldhA*)
Figure 6B:
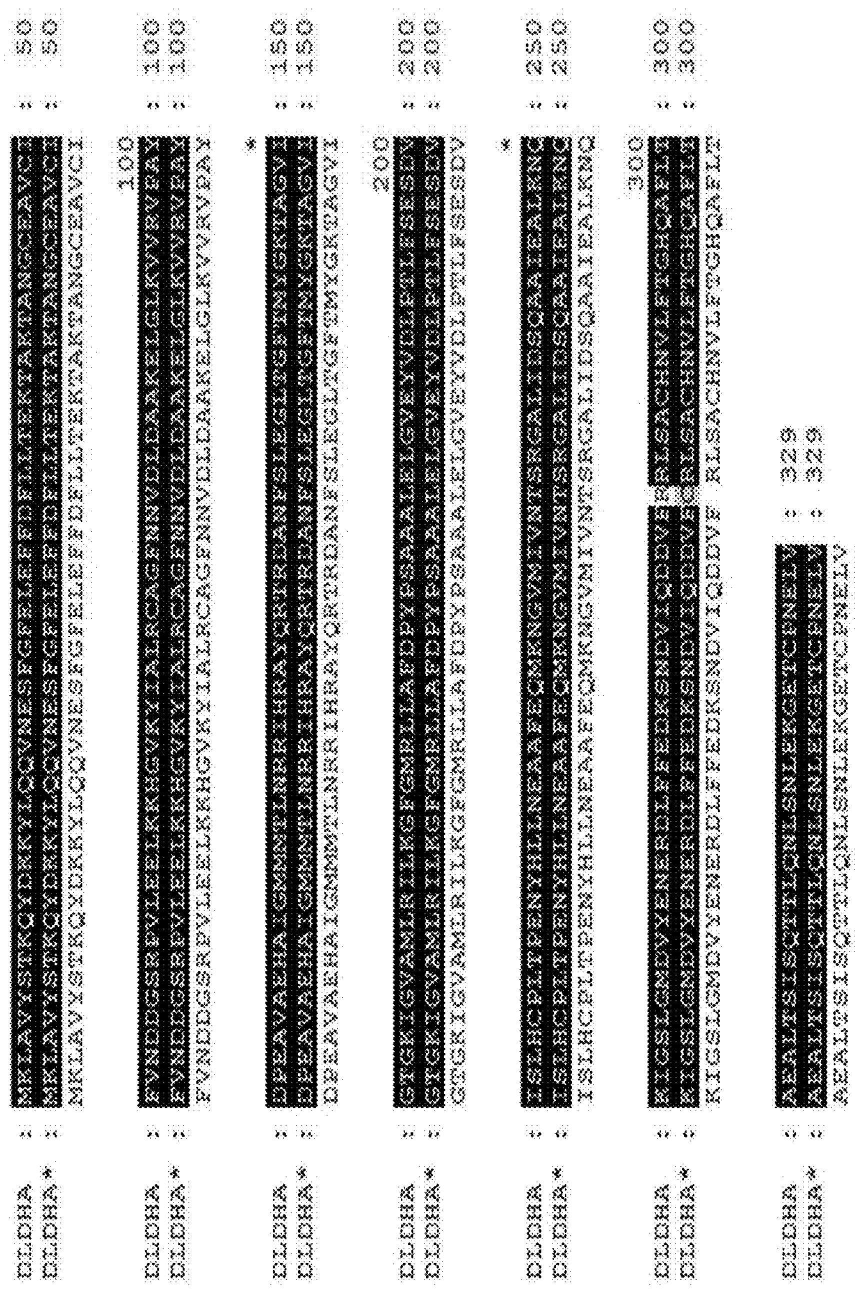
FIG. 6B shows amino acid sequence alignment of the polypeptides encoded by wild-type ldhA gene and the mutated ldhA gene (ldhA*).

In one embodiment, the invention provides a recombinant *E. coli* comprising a mutated ldhA gene, wherein said mutated ldhA gene comprises a modification at the position corresponding to position C844 of the nucleotide sequence shown in SEQ ID No.: 2, and the corresponding position is determined by sequence alignment with SEQ ID No.: 2. In one preferred embodiment, in said *E. coli*, the expression of the mutated ldhA gene is enhanced, and/or the activity of the protein encoded by said mutated ldhA gene is enhanced.

ldhA gene (GenBank No: ACA77176.1) is the gene encoding D-lactate dehydrogenase (EC No: 1.1.1.28). In one embodiment of the invention, in the used starting *E. coli* strain, the nucleotide sequence of the wild-type ldhA gene is set forth in SEQ ID No.: 2, and the amino acid sequence of the polypeptide encoded by it is set forth in SEQ ID No.: 1. In one embodiment, the mutated ldhA gene contained in the *E. coli* of the invention contains the mutation C844T (see FIG. 6A), and said mutated gene contains the sequence as set forth in SEQ ID No.: 4; while the polypeptide encoded by said mutated ldhA gene has an amino acid replacement corresponding to the mutation R282C (see FIG. 6B), and the mutated polypeptide contains the sequence as set forth in SEQ ID No.: 3.

A person skilled in the art will understand that, the ldhA gene sequences of different *E. coli* strains may be not completely identical to the ldhA gene sequence as shown in SEQ ID No.: 2, and the polypeptide sequences encoded by ldhA genes from different *E. coli* strains might be not completely identical to the polypeptide sequence as shown in SEQ ID No.: 1. In some embodiments of the invention, said mutation in the mutated ldhA gene is located at a position corresponding to position 844 of SEQ ID No.: 2. In some embodiments of the invention, the replacement in the polypeptide encoded by the mutated ldhA gene is located at a position corresponding to position 282 of SEQ ID No.: 1.

In the invention, "corresponding to" one specific position in SEQ ID No.: 1 or SEQ ID No.: 2 can be determined by sequence alignment, comprising using manual alignment, and using various available alignment programs (e.g. BLASTP), as well as other means known by a person skilled in the art. By aligning the polypeptide or nucleotide sequences, a person skilled in the art can introduce a corresponding mutation at a proper position, so as to achieve the technical effects of the invention. Besides, a person skilled in the art can also use a conservative or similar amino acid residue to replace the amino acid residue at a corresponding position, or introduce a synonymous mutation into the ldhA gene sequence, so as to achieve the technical effects of the invention In one preferred embodiment, in said *E. coli*, the expression of the mutated ldhA gene is enhanced, and/or the activity of the protein encoded by said mutated ldhA gene is enhanced.

As used herein, the term "enhanced gene expression" has the common meaning known in the art, and refers to enhancement in the intensity of gene expression, which results in an increase of the amount of mRNA generated after gene transcription. The enhanced gene expression can be achieved through the following ways, for example, but not limited to: introducing a strong promoter in front of a gene, increasing the copy number of a gene, or enhancing the stability of mRNA etc. As used herein, the term "enhanced activity of the protein encoded by a gene" has the common meaning known in the art, and refers to increase of the activity of the protein generated after gene transcription and translation. It can be achieved by e.g. enhancing the intensity of gene expression, increasing the amount of an enzyme in a cell, and introducing a mutation at an amino acid site. Various technical means used to achieve the "enhanced gene expression" and "enhanced activity of the protein encoded by a gene" are well known for a person skilled in the art.

In one embodiment, the *E. coli* of the invention contains a mutated ldhA gene, and said mutated ldhA gene is located in a plasmid.

As used herein, the term "plasmid" has a definition well known in the art, which refers to a DNA molecule that is a non-chromosome DNA existing in a cell in episome form, and capable of self-replicating. Plasmids that can be used in the invention can be e.g. pEASY-Blunt, pEASY-Blunt Simple, and pKD46 etc.

In one embodiment, the *E. coli* of the invention comprises a mutated ldhA gene, and said mutated ldhA gene is located in a chromosome.

As used herein, the term "chromosome" has a definition well known in the art. In some embodiments, the modified gene according to the invention is located in a chromosome. Techniques that can be used to integrate a modified gene into a chromosome is well known to a person skilled in the art, e.g. see Michael R. Green and Joseph Sambrook, "Molecular Cloning: A Laboratory Manual" (Fourth Edition).

In one embodiment, the *E. coli* of the invention also contains one or more of the modifications of inhibited expression of pflB gene, and/or inhibited activity of the protein encoded by pflB gene; inhibited expression of frdABCD gene cluster, and/or inhibited activity of the protein(s) encoded by frdABCD gene cluster.

In another embodiment, the *E. coli* of the invention also contains a modification selected from the modifications of inhibited expression of mgsA gene, and/or inhibited activity of the protein encoded by mgsA gene.

In the invention, pflB gene (GenBank No: ACA78322.1) encodes pyruvate formate-lyase (EC No. 2.3.1.54). The frdABCD gene cluster encodes fumarate reductase (EC No: 1.3.5.4), including frdA gene (GenBank No: ACA79460.1) encoding fumarate reductase flavoprotein subunit, frdB gene (GenBank No: ACA79461.1) encoding fumarate reductase flavoprotein subunit, frdC gene (GenBank No: ACA79462.1) encoding fumarate reductase C subunit, and frdD gene (GenBank No: ACA79463.1) encoding fumarate reductase D subunit. The mgsA gene (GenBank No: ACA78263.1) encodes methyl-glyoxal synthetase (EC No: 4.2.3.3).

As used herein, the term "inhibited gene expression" has the common meanings known in the art, and refers to the decrease in the intensity of the expression of a gene, such that the amount of mRNA generated after gene transcription is decreased. The inhibited gene expression can be achieved by the following ways, for example but not limited to: gene deletion, decreasing gene copy number, changing gene promoter (e.g. using a weak promoter) etc. As used herein, the term "inhibited activity of the protein encoded by a gene" has the common meanings known in the art, and refers to the decrease in the activity of the protein encoded by a gene. It can be achieved by, e.g. decreasing the intensity of gene expression, inserting or deleting a nucleotide in a gene, and mutating an amino acid site. Various technical means for achieving the "inhibited gene expression" and "inhibited activity of the protein encoded by a gene" are well known for a person skilled in the art.

In one embodiment, the *E. coli* of the invention is deposited in CGMCC under the deposition No. CGMCC 7678.

In one embodiment, the *E. coli* of the invention is deposited in CGMCC under the deposition No. CGMCC 7679.

In one embodiment, the *E. coli* of the invention is deposited in CGMCC under the deposition No. CGMCC 7871.

In some embodiments, the *E. coli* provided in the invention is an *E. coli* used for producing D-lactate.

The *E. coli* used for producing D-lactate refers to *E. coli* with necessary genetic backgrounds for producing D-lactate, and the necessary genetic backgrounds for producing D-lactate are well known for a person skilled in the art.

In second aspect, the invention provides a method for producing lactate, comprising the step of culturing the *E. coli* of the invention.

In one embodiment, the method for producing lactate of the invention comprises culturing the *E. coli* of the invention, and optionally collecting or purifying lactate.

In one embodiment, the "culture" of the invention includes seed culture and fermentation culture.

As used herein, the term "seed culture" refers to such a process: after activating a bacterial strain seed for fermentation on a solid medium, the activated seed is then scaled up stage by stage in shaking flask and seeding tank, so as to obtain a certain amount and quality of pure seed.

As used herein, the term "fermentation culture" refers to such a process: by using microbial strain seed, and under proper conditions, the components of medium are converted into some specific products through particular metabolic pathway(s). In one embodiment, the method of the invention for producing lactate comprises the step of performing the fermentation culture at high temperature (42-50° C.), e.g. at 42-43° C., 43-44° C., 44-45° C., 45-46° C., 46-47° C., 47-48° C., 48-49° C., or 49-50° C.

In one embodiment, the method of the invention comprises performing anaerobic fermentation of the *E. coli* of the invention.

As used herein, the term "anaerobic fermentation" refers to such a process: by using an anaerobic fermentation bacterial strain, and under anoxic conditions, the components of medium are converted into some specific products through particular metabolic pathway(s).

In one embodiment, the culture process in the method of the invention does not involve any aeration step.

In one embodiment, the method of the invention for culturing *E. coli* comprises the following steps:

(1) inoculating the recombinant *E. coli* of the invention into a seed medium, and culturing under appropriate conditions for *E. coli* for a period to obtain a seed solution;

(2) inoculating the seed solution into a fermentation medium, and culturing under anaerobic conditions.

In one embodiment, the method of the invention for producing lactate comprises the step of adjusting pH during the fermentation. In one embodiment, the method of the invention for producing lactate comprises the step of adjusting pH during the fermentation, wherein the pH is adjusted to: 6.0-8.0, e.g. 6.0-6.5, 6.5-7.0, 7.0-7.5, and 7.5-8.0. In one embodiment, the method of the invention for producing lactate comprises the step of adjusting pH using ammonia or sodium hydroxide as neutralizer during the fermentation.

In one embodiment, the method of the invention for culturing *E. coli* comprises the following steps:

(1) inoculating the recombinant *E. coli* of the invention into a seed medium, and culturing under appropriate conditions for *E. coli* for a period to obtain a seed solution;

(2) inoculating the seed solution into a fermentation medium, culturing under anaerobic conditions, and adjusting pH using ammonia or sodium hydroxide as neutralizer during the fermentation.

In one embodiment, the method of the invention for culturing *E. coli* comprises the following steps:

(1) inoculating the recombinant *E. coli* of the invention into a seed medium, and culturing under appropriate conditions for *E. coli* for a period to obtain a seed solution;

(2) inoculating the seed solution into a fermentation medium, culturing under anaerobic conditions, and adjusting pH to 6.0-8.0 using ammonia or sodium hydroxide as neutralizer during the fermentation.

In the method of the invention, various conventional culturing conditions for *E. coli* can be used, such as culture medium, culture temperature, culture time period, and whether using a shaker as well as the shaking speed etc. A person skilled in the art can choose proper conditions based one the requirements. The culturing conditions and the fermentation conditions used in the method of the invention are well known for a person skilled in the art (Zhuge, Jian et al., 1994, *Industrial Microbiology Experimental Techniques Manual*, China Light Industry Press).

In one embodiment, the culture conditions of the invention include but not limited to: the temperature is 30-50° C., e.g. 30-31° C., 31-32° C., 32-33° C., 33-34° C., 34-35° C., 35-36° C., 36-37° C., 37-38° C., 38-39° C., 39-40° C., 40-41° C., 41-42° C., 42-43° C., 43-44° C., 44-45° C., 45-46° C., 46-47° C., 47-48° C., 48-49° C., or 49-50° C.

In one embodiment, the culture conditions of the invention include but not limited to: the time period for seed culture is 6-16 hours, e.g. 6-7, 7-8, 8-9, 9-10, 10-11, 11-12, 12-13, 13-14, 14-15, or 15-16 hours.

In one embodiment, the culture conditions of the invention include but not limited to: the time period for fermentation culture is 1-5 day(s), e.g. 1 day, 2 days, 3 days, 4 days, or 5 days.

In one embodiment, the culture conditions of the invention include but not limited to: inoculating the recombinant *E. coli* of the invention into a seed medium at an inoculation amount of 0.1-10% (V/V), e.g. 0.1%, 0.5%, 1%, 2.5%, 5%, or 10%.

In one embodiment, the culture conditions of the invention include but not limited to: inoculating the seed solution into a fermentation medium at an inoculation amount of a final concentration of $OD_{550}$=0.01-0.5, e.g. with $OD_{550}$ of 0.01-0.05, 0.05-0.1, 0.1-0.2, 0.2-0.3, 0.3-0.4, or 0.4-0.5.

In one embodiment, a culture medium commonly used for *E. coli* can be used. The culture medium used for the *E. coli* of the invention can comprise a proper nitrogen source, e.g. organic nitrogen compounds, or inorganic nitrogen compounds, or mixtures thereof. In one embodiment, said organic nitrogen compounds can be e.g. selected from one or a mixture of soybean meal, peanut meal, beef extract, fish meal, yeast extract, peptone, and corn steep liquor; said inorganic nitrogen compounds can be e.g. selected from one or a mixture of nitrate salts (such as sodium nitrate, potassium nitrate, calcium nitrate), ammonium salts (such as ammonium phosphate, ammonium sulfate, ammonium nitrate, ammonium chloride). In one embodiment, the culture medium used for the *E. coli* of the invention can comprise a proper carbon source, e.g. selected from one or a mixture of glucose, starch, saccharine generated from amylohydrolysis, fructose, dextrin, lactose, galactose, xylose, sucrose, glycerol, maltose, fatty acid, acetate, pyruvate, and fumarate.

In one embodiment, the seed medium and the fermentation medium used in the method of the invention are composed of (using water as solvent):

major elements: glucose, $NH_4H_2PO_4$, $(NH_4)_2HPO_4$, $MgSO_4.7H_2O$, and betaine-HCl;

trace elements: $FeCl_3.6H_2O$, $CoCl_2.6H_2O$, $CuCl_2.2H_2O$, $ZnCl_2$, $Na_2MoO_4.2H_2O$, $MnCl_2.4H_2O_2$, and $H_3BO_3$.

In one embodiment, the culture medium of the invention is composed of (using water as solvent):

major elements: glucose 20-140 g/L, $NH_4H_2PO_4$ 0.5-1.5 g/L, $(NH_4)_2HPO_4$ 2-5 g/L, $MgSO_4.7H_2O$ 0.1-0.3 g/L, and betaine-HCl 0.1-1 g/L;

trace elements: $FeCl_3.6H_2O$ 1-5 μg/L, $CoCl_2.6H_2O$ 0.05-1 μg/L, $CuCl_2.2H_2O$ 0.05-1 μg/L, $ZnCl_2$ 0.05-1 μg/L, $Na_2MoO_4.2H_2O$ 0.05-1 μg/L, $MnCl_2.4H_2O_2$ 0.1-1 μg/L, and $H_3BO_3$ 0.01-0.5 μg/L.

In one embodiment, the method of the invention for culturing *E. coli* is specifically as following:

anaerobic fermentation of bacteria strain, comprising the following steps:

(1) seed culture: placing ⅓-½ volume of seed medium into a triangular flask, and autoclaving for sterilization. After cooling down, inoculating the recombinant *E. coli* of the invention at an inoculation amount of 0.1-10% (V/V) into the seed medium, and culturing at 37° C. or 42° C. for 6-16 hours under shaking to obtain a seed solution for inoculating fermentation medium;

(2) fermentation culture: placing ⅓-½ volume of fermentation medium into an anaerobic fermentor, inoculating the seed solution into the fermentation medium at an inoculation amount of a final concentration of $OD_{550}$=0.01-0.5, and culturing at 37° C. or 42° C. for 1-5 days, to obtain fermentation broth.

In one embodiment, the method of the invention for producing lactate further comprises the step of extracting and/or purifying lactate from the fermentation broth.

In one embodiment, the method of the invention comprises the following steps:

(1) culturing the *E. coli* of the invention in fermentation; and (2) collecting the produced D-lactate; and optionally isolating or purifying D-lactate.

In third aspect, the invention relates to use of the *E. coli* of the invention in the production of lactate.

EXAMPLES

The invention is further illustrated through the following examples, but any example or combination thereof should not be construed as limiting the scope or embodiment of the invention. The scope of the invention is defined by the attached claims, and based on the present specification and common knowledge in the art, a person skilled in the art can clearly understand the scope as defined by the claims. As long as the spirit and scope of the invention is obeyed, a person skilled in the art can make any modifications or changes to the technical solutions of the invention, and such modifications or changes are also included into the scope of the invention.

The experiments in the following examples are all conventional processes, unless otherwise indicated. The material, reagents etc. used in the following examples are all commercially available, unless otherwise indicated.

The invention comprises the following examples:

Example 1

Construction of Recombinant *E. coli* Dlac-006

Construction of recombinant *E. coli* Dlac-006 (Table 1) comprised following three steps:

(1) Deletion of Pyruvate Formate Lysase Gene pflB (1-1): construction of plasmid pXZ-CS for gene deletion, gene modulation and integration of exogenous genes.

The construction of the plasmid included four steps:

First step, a chloramphenicol resistance gene was amplified by using the plasmid pACYC184 DNA (Mok et al., 1991. Nucleic acids Res 19:2321-2323) as template with primer set 184-cat-up (SEQ ID No.: 5) and 184-cat-down (SEQ ID No.: 6). The amplified chloramphenicol resistance gene was 994 by in size, and contained the chloramphenicol gene promoter sequence, designated as fragment I.

PCR system: 10 μl of New England Biolabs Phusion 5× buffer, 1 μl of dNTP (10 mM of each dNTP), 20 ng of DNA template, 2 μl of each primer (each of 10 μM), 0.5 μl of Phusion High-Fidelity DNA polymerase (2.5 U/μL), 33.5 μl of distilled water, in 50 μl of total volume.

PCR cycles: 1 cycle of 98° C. for 2 minutes (predenaturing); 30 cycles of 98° C. for 10 seconds (denaturing), 56° C. for 10 seconds (annealing), and 72° C. for 30 seconds (extension); 1 cycle of 72° C. for 5 minutes (extension).

Second step, a levansucrase gene (sacB) was PCR amplified by using the chromosome DNA from *Bacillus subtilis* sp subtilis 168 (purchased from China General Microbiological Culture Collection Center; CGMCC No. 1.1390) as template with primer set Bs-sacB-up (SEQ ID No.: 7) and Bs-sacB-down (SEQ ID No.: 8). The resulting PCR product was 1618 by in size, and contained sacB gene promoter sequence, designated as fragment II. The PCR system and cycles were referred to the first step described above.

Third step, fragment I obtained in the first step and fragment II obtained in the second step were digested with restriction endonuclease SacI (NEB company) at 37° C. for 30 minutes. The digested products were cleaned using PCR purification kit Gel/PCR Extraction kit (BioMIGA Biotechnology Company). Each 20 ng of fragment I and fragment II were added with 1 μl of 10XT4-DNA ligase buffer (NEB) and 1 μl of T4-DNA ligase (NEB), supplemented with distilled water to a total volume of 10 μl, and reacted at 25° C. for 5 minutes. Taking 1 μl of ligation product as template, fragment III containing cat-sacB cassette was amplified with a primer set 184-cat-up/Bs-sacB-down. The PCR system and Cycles were referred to the first step described above.

Fourth step, 1 μl of fragment III obtained from PCR was mixed with 1 μl of pEASY-blunt simple vector (Beijing TransGen Biotech, China) and reacted at 25° C. for 15 min. $CaCl_2$ transformation: adding 50 μl of Trans10 Competent Cells (Beijing TransGen Biotech, China) and in ice-bath for 30 min; heat shocking at 42° C. for 30 seconds, and immediately transferring on ice for 2 minutes. Adding 250 μl of LB medium and incubating at 37° C., 200 rpm for 1 hour. 200 μl of transformed competent cells were plated onto a LB plate containing ampicillin (final concentration of 100 μg/mL) and chloramphenicol (final concentration of 34 μg/mL). After grown overnight, 5 positive colonies were PCR verified with primer set M13-F (SEQ ID No.: 9)/M13-R (SEQ ID No.: 10) and sequenced. The correct plasmid was designated as pXZ-CS (Table 3).

(1-2): Starting from *E. coli* ATCC 8739 (Gunsalus et al., 1941, J Biol Chem 141:853-858), recombinant *E. coli* strain Dlac-002 was constructed by deleting pflB gene using a two-step homologous recombination method. Six steps were included as described below:

First step, using the genomic DNA of *E. coli* ATCC 8739 as template, a 2260 by fragment was PCR amplified with primer set XZ-pflB-up (SEQ ID No.: 11) and XZ-pflB-down (SEQ ID No.: 12). This PCR product contained pyruvate formate lysase gene pflB (GenBank No: ACA78322.1) of *E. coli* ATCC 8739 and its upstream and downstream sequences of about 400 bp. The PCR system and cycles were referred to the first step in section (1-1) of Example 1 described above.

The 2260 by PCR product was then cloned into pEASY-Blunt cloning vector (Beijing TransGen Biotech). The cloning system and calcium chloride transformation were referred to the fourth step in the above section (1-1) for the construction of plasmid pXZ-CS. 200 μl of transformed competent cells were plated onto a LB plate containing kanamycin (final concentration of 50 μg/ml). After grown overnight, 5 positive colonies were verified by colony PCR with primer set M13-F/M13-R and sequenced. The correct plasmid was designated as pXZ-014.

Second step, using plasmid pXZ014 as template, a 4828 by PCR product was amplified with primer set XZ-pflB-1 (SEQ ID No.: 13) and XZ-pflB-2 (SEQ ID No.: 14). This PCR product contained pEASY-Blunt vector and each of the upstream and downstream sequences of pyruvate formate lysase gene of about 400 bp. The PCR system and cycles were referred to the first step in section (1-1) of Example 1 described above.

Third step, the DNA fragment cat-sacB containing chloramphenicol gene (cat) and levansucrase gene (sacB) was ligated into the PCR amplified product of the second step. The details were as follows:

Using pXZ-CS as template, a 2618 by PCR fragment was PCR amplified with primer set cat-sacB-up (SEQ ID No.: 15) and cat-sacB-down (SEQ ID No.: 16). This PCR product was the DNA fragment which contained chloramphenicol gene (cat) and levansucrase gene (sacB).

Ligation system: 10 ng pf the 4828 by PCR fragment obtained in the second step, 30 ng of cat-sacB cassette DNA fragment, 2 μl of 10XT4 ligation buffer (NEB company), 1 μl of T4 ligase (NEB Company, 400,000 cohesive end units/ml), and supplemented distilled water to a final volume of 20 μl. The ligation reaction was carried out at room temperature for 2 hours and 10 μl of ligation product were transformed into Trans10 by $CaCl_2$ transformation method. The transformation steps were referred to the fourth step described in the above section (1-1) for construction of plasmid pXZ-CS. 200 μl of the transformed competent cells were plated onto a LB plate containing chloramphenicol (final concentration of 34 μg/mL). After grown overnight, 5 positive clones were selected and cultured in liquid medium. Positive plasmids (cat-sacBDNA fragment was cloned into the plasmid pXZ014) were then extracted and verified by sequencing. The sequencing results showed that cat-sacB DNA fragment was ligated to the PCR product in the above second step and this demonstrated that the plasmid was constructed correctly. The obtained recombinant plasmid was designated as pXZ015C.

Fourth step, using plasmid pXZ015C DNA as template, a 3515 by DNA fragment I was amplified with primer set XZ-pflB-up/XZ-pflB-down. The PCR system and cycles were referred to the first step in section (1-1) as described above for construction of plasmid pXZ-CS. The DNA fragment I contained about 400 by upstream of pyruvate formate lysase gene pflB, cat-sacB cassette DNA fragment, and about 400 by downstream of pyruvate formate lysase gene pflB.

The DNA fragment I was used for the first homologous recombination: First, plasmid pKD46 (Wanner and Datsenko 2000, Proc Natl Acad Sci USA 97:6640-6645; plasmid was purchased from Yale University CGSC *E. coli* Depositary Center, CGSC#7739) was transformed into *E. coli* ATCC 8739 by $CaCl_2$ transformation, and then the DNA fragment I was electroporated into *E. coli* ATCC 8739 harboring the pKD46.

Electroporation process: first, electroporation competent cells of *E. coli* ATCC 8739 harboring the pKD46 were prepared by the method described by Dower (Dower et al., 1988. Nucleic Acids Res 16:6127-6145). 50 ng of the DNA fragment I was added into 50 μl of electroporation competent cells which were placed on ice. The mixture was then placed on ice for 2 minutes and transferred into a 0.2 cm MicroPulser Electroporation Cuvette (Bio-Rad). The electroporation was carried with the MicroPulser (Bio-Rad) electroporation apparatus and the electric voltage was 2.5 kV. After shock, lmL of LB medium were quickly added into the electroporation cuvette and transferred into a tube after pipetting five times. The culture was incubated at 30° C. with shaking at 75 rpm for two hours. 200 μl of culture was spread onto a LB plate containing chloramphenicol (final concentration of 34 μg/mL), and incubated at 37° C. overnight. Five colonies were PCR verified with primer set XZ-pflB-up/XZ-pflB-down. A correct colony was selected and designated as Dlac-001.

Fifth step, the 4828 by PCR product obtained in the second step was phosphorylated, and the self-ligated plasmid was used for the second homologous recombination. The details were as follows: 4818 by PCR product obtained in the second step was first cleaned using the PCR purification kit (Gel/PCR Extraction Kit, BioMIGA). 30 ng purified PCR amplified product was then added into 2 μl 10XT4 ligation buffer (NEB), 1 μl of T4 polynucleotide kinase (NEB), and distilled water was supplemented to reach a final volume of 204 The reaction was carried out at 37° C. for 30 minutes. Then, 1 μl of T4 ligase (NEB, 400,000 cohesive end units/ml) was added into the mixture and ligation reaction were carried out at room temperature for 2 hours to obtain the ligation product. 10 μl of the ligation product was transformed into Trans10 using $CaCl_2$ transformation method, referring to the fourth step described in the above section (1-1) for construction of plasmid pXZ-CS. 200 μl of transformed competent cells were spread onto a LB plate containing kanamycin (final concentration of 50 μg/mL). After grown overnight, 5 positive colonies were picked up and cultured in liquid medium. The positive plasmids were then extracted and verified by sequencing. The sequencing results showed that the PCR product obtained in the second step was self-ligated and this indicated that the plasmid was constructed correctly which was then designated as pXZ016.

Sixth step, using plasmid pXZ016 DNA as template, a 897 by DNA fragment II was amplified with primer set XZ-pflB-up/XZ-pflB-down. DNA fragment II was used for the second homologous recombination and was electroporated into the strain Dlac-001.

Electroporation process: first, electroporation competent cells of Dlac-001 harboring the pKD46 were prepared by the method described by Dower (Dower et al., 1988). 50 ng of the DNA fragment II was added into 50 μl of electroporation competent cells which were placed on ice. The mixture were then placed on ice for 2 minutes and transferred into a 0.2 cm MicroPulser Electroporation Cuvette (Bio-Rad). The electroporation was carried with the MicroPulser (Bio-Rad) electroporation apparatus and the electric voltage was 2.5 kV. After shock, lmL of LB medium were quickly added into the electroporation cuvette and transferred into a tube after pipetting five times. The culture was incubated at 30° C. with shaking at 75 rpm for four hours. The culture was then transferred into LB medium with 10% sucrose but without sodium chloride (50 mL medium in 250 mL flask), cultured for 24 hours and then streaked on LB solid medium with 6% sucrose but without sodium chloride and incubated. The correct clone was verified by colony PCR amplification with primer set XZ-ldhA-up/XZ-ldhA-down and the correct colony amplification product was a fragment of 897 bp. The correct colony was then picked out and designated as Dlac-002 (Table 1).

Plasmids constructed for deletion of pflB gene were listed in Table 3 and the primers used were listed in Table 2.

(2) Deletion of Fumarate Reductase Gene frdABCD

Fumarate reductase gene frdABCD (frdAGenBank No: ACA79460.1, frdB GenBank No: ACA79461.1, frdC GenBank No: ACA79462.1, frdD GenBank No: ACA79463.1) of recombinant *E. coli* Dlac-002 was deleted using the same method as described in Example 1 (1-2) and the resulting recombinant *E. coli* strain was named as Dlac-004. Plasmids constructed were listed in Table 3 and the primers used were listed in Table 2. The primers were named in the same manner as those used for deleting pflB gene, while only pflB was replaced by frdB or frdC.

(3) Deletion of Methylglyoxal Synthase Gene mgsA

Methylglyoxal synthase gene mgsA (GenBank No:ACA78263.1) of recombinant *E. coli* Dlac-004 was deleted using the same method as described in Example 1 (1-2) and the resulting recombinant *E. coli* strain was named as Dlac-006. Plasmids constructed were listed in Table 3 and the primers used were listed in Table 2. The primers were named in the same manner as those used for deleting pflB gene, while only pflB was replaced by mgsA.

TABLE 1

Recombinant *E. coli* strains for producing D-lactate

| Strains | Relevant characteristics |
|---|---|
| ATCC 8739 | Wild type |
| Dlac-002 | ATCC 8739, ΔpflB |
| Dlac-004 | ATCC 8739, ΔpflB, ΔfrdABCD |
| Dlac-006 | ATCC 8739, ΔpflB, ΔfrdABCD, ΔmgsA |
| Dlac-012 | Metabolic evolution of Dlac-006 for 520 generations. Deposited in CGMCC with CGMCC 7678 |
| Dlac-014 | Dlac-012, the deleted mgsA gene was restored to wild type, deposited in CGMCC with CGMCC 7871 |
| Dlac-206 | Metabolic evolution of Dlac-012 for 360 generations. Deposited in CGMCC with CGMCC 7679 |

TABLE 2

Primers used in the invention

| Name | sequences |
|---|---|
| **Construction of pXZ-CS** | |
| 184-cat-up | GCTAGGTACCTGTGACGGAAGATCACTTCG (SEQ ID No.: 5) |
| 184-cat-down | GCTAGAGCTCGCGGCTATTTAACGACCCT (SacI) (SEQ ID No.: 6) |
| Bs-sacB-up | GCTAGAGCTCAAGTAAATCGCGCGGGTTT (SacI) (SEQ ID No.: 7) |
| Bs-sacB-down | GCTAGGATCCTTATTTGTTAACTGTTAATTGTC (SEQ ID No.: 8) |
| M13-F | GTAAAACGACGGCCAGT (SEQ ID No.: 9) |

TABLE 2-continued

Primers used in the invention

| Name | sequences |
|---|---|
| M13-R | CAGGAAACAGCTATGAC (SEQ ID No.: 10) |
| **Deletion of pflB gene** | |
| XZ-pflB-up | TGTCCGAGCTTAATGAAAAGTT (SEQ ID No.: 11) |
| XZ-pflB-down | CGAGTAATAACGTCCTGCTGCT (SEQ ID No.: 12) |
| XZ-pflB-1 | AAACGGGTAACACCCCAGAC (SEQ ID No.: 13) |
| XZ-pflB-2 | CGGAGTGTAAACGTCGAACA (SEQ ID No.: 14) |
| cat-sacB-up | TGTGACGGAAGATCACTTCGCA (SEQ ID No.: 15) |
| cat-sacB-down | TTATTTGTTAACTGTTAATTGTCCT (SEQ ID No.: 16) |
| **Deletion of frd gene** | |
| XZ-frdB-up | TGCAGAAAACCATCGACAAG (SEQ ID No.: 17) |
| XZ-frdC-down | CACCAATCAGCGTGACAACT (SEQ ID No.: 18) |
| XZ-frdC-1 | GCCACCATCGTAATCCTGTT (SEQ ID No.: 19) |
| XZ-frdB-2 | ATAGCGCACCACCTCAATTT (SEQ ID No.: 20) |
| **Deletion of mgsA gene** | |
| XZ-mgsA-up | CAGCTCATCAACCAGGTCAA (SEQ ID No.: 21) |
| XZ-mgsA-down | AAAAGCCGTCACGTTATTGG (SEQ ID No.: 22) |
| XZ-mgsA-1 | AGCGTTATCTCGCGGACCGT (SEQ ID No.: 23) |
| XZ-mgsA-2 | AAGTGCGAGTCGTCAGTTCC (SEQ ID No.: 24) |

TABLE 3

| Plasmids constructed in the invention | |
|---|---|
| Plasmids | Relevant characteristics |
| | Plasmid with cat-sacB cassette |
| pXZ-CS | Cat gene of the plasmid pACYC184 and sacB gene from *Bacillus subtilis* were ligated and cloned into the plasmid pEASY-Blunt simple |
| | pflB gene deletion |
| pXZ014 | pflB gene was PCR amplified by using *E. coli* ATCC 8739 genome as template with primer set XZ-pflB-up/XZ-pflB-down and cloned into pEASY-Blunt vector |
| pXZ015C | cat-sacB cassette was PCR amplified by using pXZ-CS as template with primer set cat-sacB-up/cat-sacB-down and cloned into the DNA fragment amplified by using the plasmid pXZ014 as template with primer set XZ-pflB-1/ XZ-pflB-2 |
| pXZ016 | PCR fragment amplified by using plasmid pXZ014 DNA as template with primer set XZ-pflB-1/XZ-pflB-2 was phosphorylated and self-ligated |
| | frd gene deletion |
| pXZ005 | frdABCD gene was PCR amplified by using *E. coli* ATCC 8739 genome as template with primer set XZ-frdB-up/XZ-frdC-down and cloned into pEASY-Blunt vector |
| pXZOO6C | cat-sacB cassette was PCR amplified by using pXZ-CS as template with primer set cat-sacB-up/cat-sacB-down and cloned into the DNA fragment amplified by using the plasmid pXZ005 DNA as template with primer set XZ-frdC-1/XZ-frdB-2 |
| pXZ007 | PCR fragment amplified by using plasmid pXZ005 DNA as template with primer set XZ-frdC-1/XZ-frdB-2 was phosphorylated and self-ligated |
| | mgsA gene deletion |
| pXZ071 | mgsA gene was PCR amplified by using *E. coli* ATCC 8739 genome as template with primer set XZ-mgsA-up/XZ-mgsA-down and cloned into pEASY-Blunt vector |
| pXZ072C | cat-sacB cassette was PCR amplified by using pXZ-CS as template with primer set cat-sacB-up/cat-sacB-down and cloned into the DNA fragment amplified by using the plasmid pXZ071 as template with primer set XZ-mgsA-1/XZ-mgsA-2 |
| pXZ073 | PCR fragment amplified by using plasmid pXZ071 as template with primer set XZ-mgsA-1/XZ-mgsA-2 was phosphorylated and self-ligated |

Example 2

Production of D-Lactate by Using Recombinant *E. coli* Dlac-002, Dlac-004 and Dlac-006

The seed medium consisted of ($H_2O$ as solvent):

Major elements: glucose 20 g/L, $NH_4H_2PO_4$ 0.87 g/L, $(NH_4)_2HPO_4$ 2.63 g/L, $MgSO_4$. $7H_2O$ 0.18 g/L and betaine-HCl 0.15 g/L.

Trace elements: $FeCl_3.6H_2O$ 1.5 μg/L, $CoCl_2.6H_2O$ 0.1 μg/L, $CuCl_2.2H_2O$ 0.1 μg/L, $ZnCl_2$ 0.1 μg/L, $Na_2MoO_4.2H_2O$ 0.1 μg/L, $MnCl_2.4H_2O$ 0.2 μg/L, $H_3BO_3$ 0.05 μg/L.

Fermentation medium was the same as the seed medium, except for containing 100 g/L glucose.

The anaerobic fermentation of Dlac-002, Dlac-004 and Dlac-006 included following steps:

(1) Seed culture: 100 ml of seed medium in a 250 ml flask was sterilized at 115° C. for 15 min. After cooling, Dlac-002, Dlac-004 and Dlac-006 were grown by transferring the pre-inocula (an inoculum of 1% (v/v)) into the seed medium, at 37° C. with shaking at 100 rpm for 12 h to obtain the seed culture used for inculation in fermentation medium.

(2) Fermentation culture: the seed cultures were inoculated into a 500-ml fermentation vessel containing 250 ml of fermentation medium with a final concentration of $OD_{550}$=0.1, and grown at 37° C., 150 rpm for 2 days to obtain the fermentation broth. The fermentative pH was controlled at 7.0 by adding 5 M ammonia as neutralizer. The fermentation broth comprises all the substance in the vessel. No air was sparged during the fermentation.

Analysis method: the components in the fermentation broth after fermentation for 48 hours were assayed by using High-Performance Liquid Chromatograph (Agilent-1200). The concentrations of glucose and organic acids in the fermentation broth were measured by the column Aminex HPX-87H (Bio-rad). The optical purity of lactate was analyzed using the column SUMICHIRAL OA-6000 (Sumika Chemical Analysis Service). The results were shown in Table 4.

Figure 1:
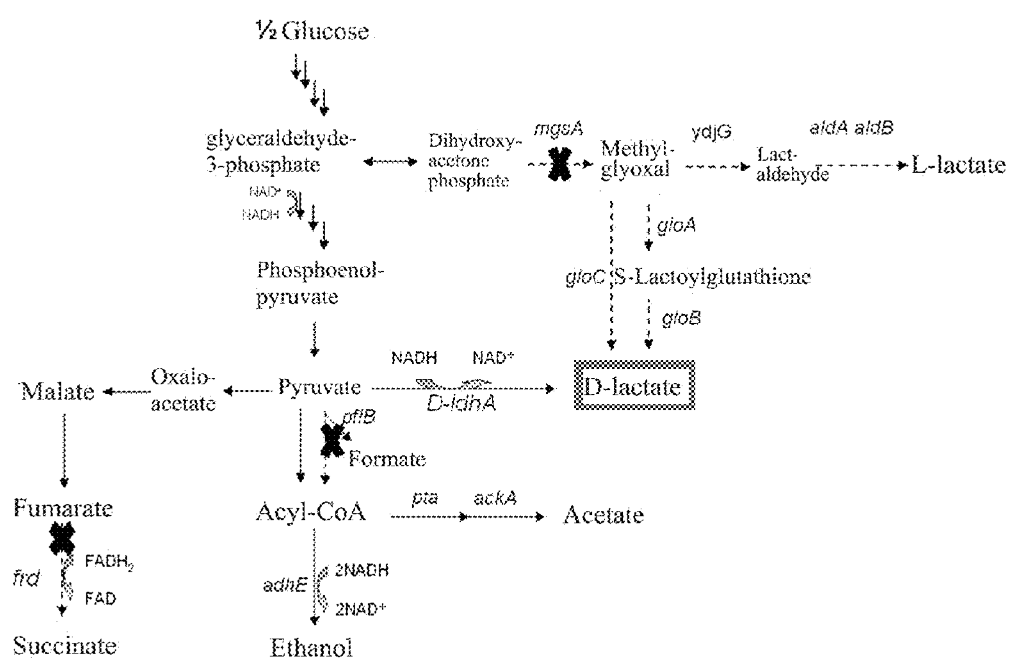
FIG. 1: schematic diagram for modifying *E. coli* to obtain the recombinant bacterial strain Dlac-006. X represents gene deletion, including deleting genes pflB, frd, and mgsA.
Figure 2:
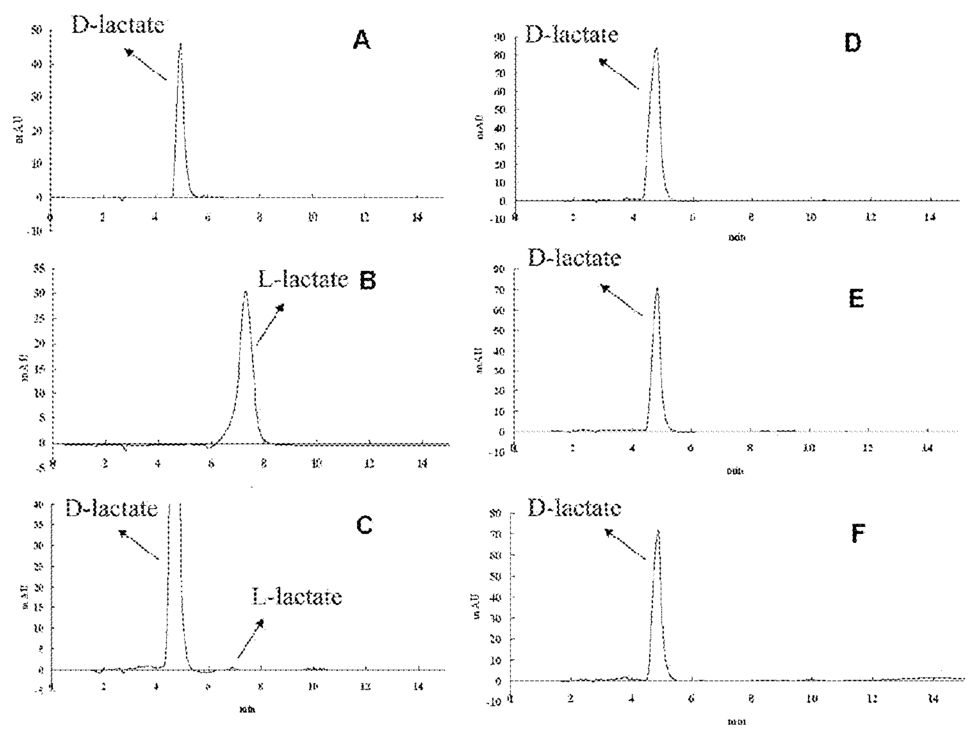
FIG. 2: the optical purity of D-lactate produced by the fermentation of strains Dlac-002, Dlac-004, and Dlac-006.

The results were shown in FIG. 2. L-lactate was not detected in the fermentation broth of Dlac-002, Dlac-004 and Dlac-004 when analyzed using HPLC. The optical purity of D-lactate was higher than 99.5%. As shown in FIG. 2, FIG. 2A was the standard of D-lactate, FIG. 2B was the standard of L-lactate, FIG. 2C was the mixture of D-lactate and L-lactate (the optical purity of D-lactate was 99.5%), FIG. 2D was Dlac-002, FIG. 2E was Dlac-004, and FIG. 2F was Dlac-006.

TABLE 4

Production of lactate by recombinant *E. coli* strains

| Strain[a] | Genetic modification | Cell mass (g/L) | D-lactate yield (mol/mol) | Optical purity of D-lactate | Fermentative products (mM) lactate | succinate |
|---|---|---|---|---|---|---|
| Dlac-002 | ATCC 8739, ΔpflB, | 1.95 | 1.88 | >99.5% | 1044 | 13 |
| Dlac-004 | ATCC 8739, ΔpflB, ΔfrdABCD | 1.02 | 1.94 | >99.5% | 493 | 0 |
| Dlac-006 | ATCC 8739, ΔpflB, ΔfrdABCD, ΔmgsA | 0.85 | 1.92 | >99.5% | 317 | 0 |
| Dlac-012 | Metabolic evolution of Dlac-006 for 520 generations (containing ldhA*) | 3.0 | 1.88 | >99.5% | 1460 | 0 |
| Dlac-014 | Dlac-012, the deleted mgsA gene was restored to wild type | 0.99 | 1.62 | >99.5% | 800 | 0 |
| Dlac-206 | High-temperature tolerant strain obtained by metabolic evolution of Dlac-012 for 360 generations | 2.41 | 1.94 | >99.5% | 1133 | 0 |

[a]500-ml fermentation vessel, 250 ml fermentation medium. 5M ammonia was used as neutralizer to control the pH at 7.0.

Example 3

Construction of Recombinant *E. coli* Dlac-012

Cell growth and D-lactate production were improved by metabolic evolution of strain Dlac-006.

Fermentation medium used for metabolic evolution consisted of the following components ($H_2O$ as solvent):

Major elements: glucose 100-140 g/L, $NH_4H_2PO_4$ 0.87 g/L, $(NH_4)_2HPO_4$ 2.63 g/L, $MgSO_4.7H_2O$ 0.18 g/L and betaine-HCl 0.15 g/L.

Trace elements: $FeCl_3.6H_2O$ 2.4 μg/L, $CoCl_2.6H_2O$ 0.3 μg/L, $CuCl_2.2H_2O$ 0.15 μg/L, $ZnCl_2$ 0.3 μg/L, $Na_2MoO_4.2H_2O$ 0.3 μg/L, $MnCl_2.4H_2O$ 0.5 μg/L, $H_3BO_3$ 0.072 μg/L.

Metabolic evolution was carried out in 500 mL fermentation vessel containing 250 mL fermentation medium. The fermentative pH was controlled at 7.0 by using 5 M ammonia as neutralizer.

For 1-250 generations, the concentration of glucose in fermentation medium was 100 g/L (10%); Every 24 hours, the fermentation broth was transferred into a new fermentation vessel and the initial OD550 was 0.05.

For 250-340 generations, the concentration of glucose in fermentation medium was 120 g/L (12%); Every 24 hours, the fermentation broth was transferred into a new fermentation vessel and the initial OD550 was 0.05.

For 340-430 generations, the concentration of glucose in fermentation medium was 130 g/L (13%); Every 24 hours, the fermentation broth was transferred into a new fermentation vessel and the initial OD550 was 0.05.

For 430-520 generations, the concentration of glucose in fermentation medium was 140 g/L (14%); Every 24 hours, the fermentation broth was transferred into a new fermentation vessel and the initial OD550 was 0.05.

Figure 3:
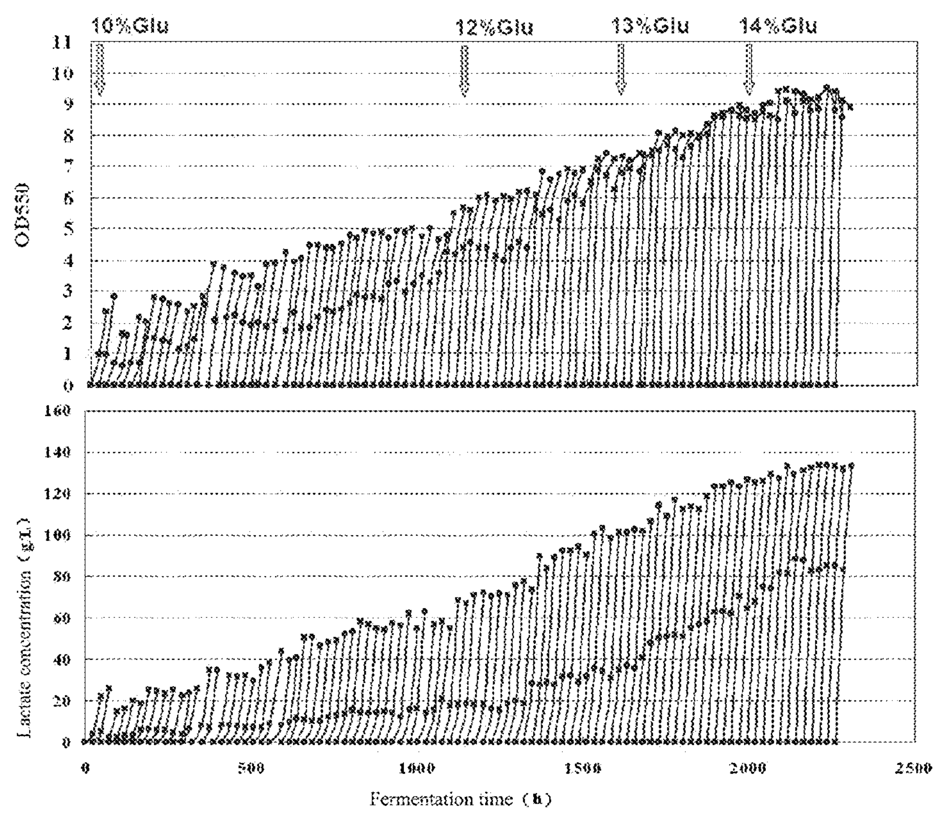
FIG. 3: The bacterial strain Dlac-012 obtained from Dlac-006 by evolution for 520 generations.

After 520 generations, strain Dlac-012 was obtained (FIG. 3). Dla-012 was deposited in CGMCC with CGMCC 7678.

Example 4

Fermentation of Recombinant *E. coli* Dlac-012 in 500 mL Fermentation Vessel The seed medium was the same as that described in Example 3.

The fermentation was carried out in 500 mL fermentation vessel containing 250 mL fermentation medium. The Fermentation medium was the same as the seed medium, except that the concentration of glucose was 140 g/L. 5 M ammonia was used as neutralizer to control the pH at 7.0.

Figure 4:
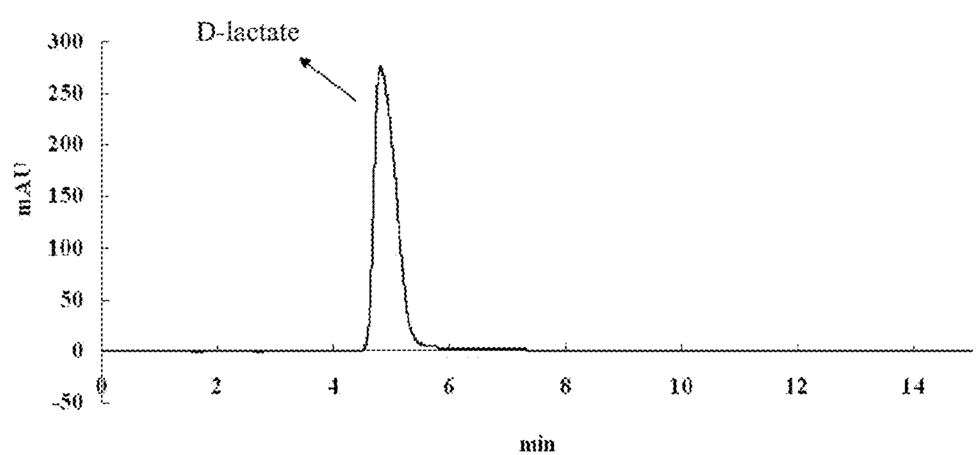
FIG. 4: the optical purity of D-lactate produced by Dlac-012 in 500 mL fermentor.

Results: After fermentation for 48 hours, Dlac-012 produced 1460 mM D-lactate. The D-lactate yield was 1.88 mol/mol (Table 4), and the optical purity was higher than 99.5% (FIG. 4).

Example 5

Fermentation of Recombinant *E. coli* Dlac-012 in 5 L Fermentation Vessel

The seed medium and analysis method were same as described in Example 3. The Fermentation medium was the same as the seed medium, except that the concentration of glucose was 140 g/L.

The anaerobic fermentation of Dlac-012 in 5 L fermentation vessel (Shanghai BaoXing, BIOTECH-5BG) included following steps:

(1) Seed culture: 150 ml of seed medium in a 500 ml flask was sterilized at 115° C. for 15 min. After cooling, recombinant *E. coli* Dlac-012 was grown by transferring pre-inocula (an inoculum of 1% (v/v)) into the seed medium, at 37° C. with shaking at 100 rpm for 12 h to obtain the seed culture used for inoculating into fermentation medium.

(2) Fermentation culture: 3 L of fermentation medium in a 5 L fermentation vessel was sterilized at 115° C. for 25 min. The seed culture was inoculated into the fermentation medium with a final concentration of $OD_{550}$=0.2, and grown at 37° C., 200 rpm under anaerobic condition for 2 days to obtain the fermentation broth. The fermentation broth comprises all the substance in the vessel. No air was sparged during the fermentation.

Figure 5A:
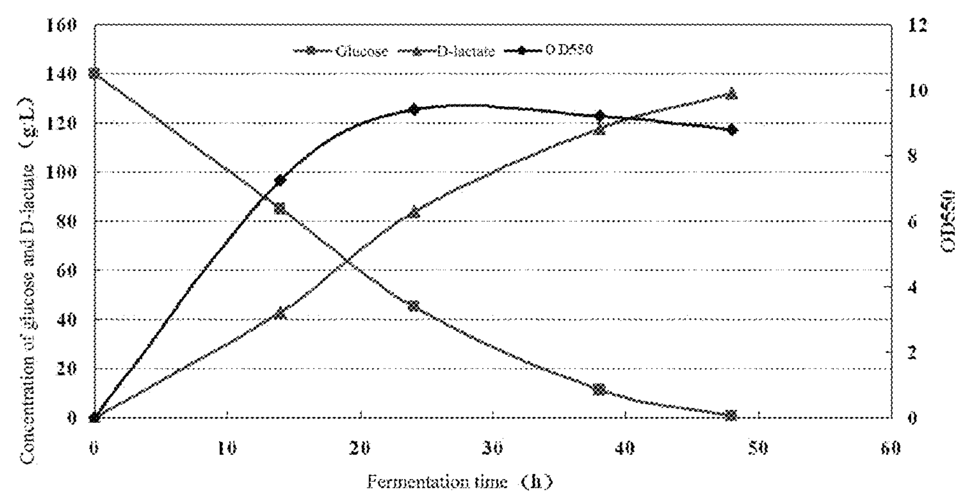
FIG. 5A shows cell growth, glucose consumption, and the production of D-lactate.
Figure 5B:
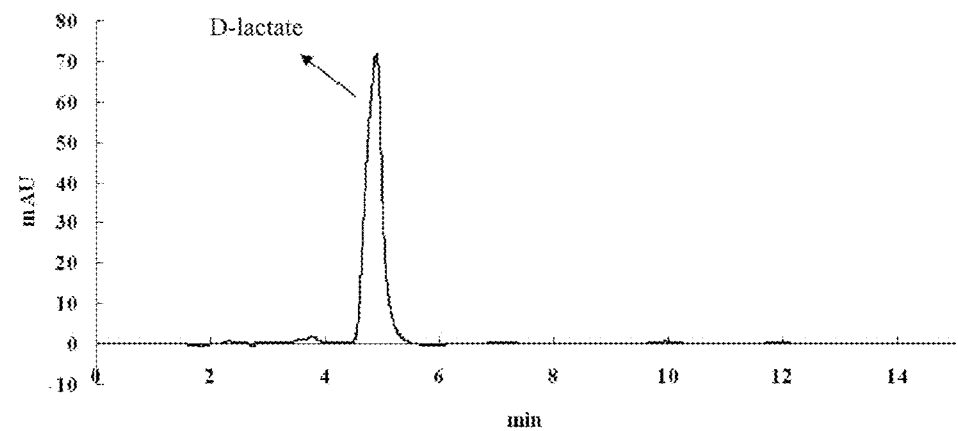
FIG. 5B shows the optical purity of D-lactate produced by fermentation.

Results were shown as FIG. 5: After fermentation for 48 hours, the titer of D-lactate was 1478 mM (equivalent to 133 g/L), the yield was 1.9 mol/mol (equivalent to 0.95 g/g), and the optical purity of D-lactate was higher than 99.5%.

Example 6

Genomics Analysis of Recombinant *E. coli* Dlac-012

Recombinant *E. coli* Dlac-012 was analyzed using Genome sequencing. Following steps were included:

(1) Fermentation

The seed culture and fermentation were the same as Example 3. Three parallel anaerobic fermentations were performed.

(2) Preparation of Dlac-012 Genome

Three parallel fermentation samples were collected at OD550=3.2, mixed and extracted for bacteria genomic DNA using Wizard® Genomic DNA Purification Kit (Promega). The concentration of DNA was measured by Qubit Fluorometer and quantitative agarose gel electrophoresis.

(3) Genome Resequencing

Genome resequencing was finished by BGI (Beijing, China). The Paired-End fragments library was constructed by whole-genome shotgun and used for sequencing. The sequencing overall depth was at least 100 times and the expected clean data was 500 Mbp. The technical methods and routes used for sequencing were: Preparation of DNA samples—sequencing—data processing—bioinformatics analysis. The reference sequence was the genomic sequence of ATCC 8739 www.ncbi.nlm.nih.gov/nuccore/NC_010468.1).

Results of the genome sequencing: Genome sequencing analysis showed that except for the genetic modifications mentioned in above Examples, only one gene contained mutation. This gene was D-lactate dehydrogenase and the mutation was the mutation of C at position 844 in the nucleotide sequence to T (FIG. 6). This gene was named as ldhA*.

Example 7

Enzyme Assay of Recombinant *E. coli* Dlac-012

Enzyme assays of recombinant *E. coli* Dlac-006 and Dlac-012 were carried out as follows:

(1) Fermentation

The seed culture and fermentation of Dlac-006 were the same as described in Example 2.

The seed culture and fermentation of Dlac-012 were the same as described in Example 4.

(2) Cell Extract Preparation

Cells were grown to exponential phase. 15 mL of fermentation broth at exponential phase were centrifuged and collected at 4° C. The cells were washed for 2 times with pre-cold Tris-HCl (pH7.5) and then re-suspended in 1.5 mL Tris-HCl (pH7.5). Cells were disrupted by ultrasonic cell crusher (SCIENTZ-II0, Ningbo Scientz Biotechnology Co. Ltd, China) with ultrasonic intensity of 30% for 7 min (On: 1 Sec; Off: 2 Sec). Finally, cell debris was removed by centrifuged at 4° C., 10,000 rpm for 20 min.

Determination of the total protein concentration in cell extracts: the total protein concentration in cell extracts was determined with Bio-Rad Protein Assay Kit (Bio-Rad) and operation was according to the instructions provided by the Kit.

(3) Enzyme Assay for D-Lactate Dehydrogenase, LdhA 1 mL reaction mixture included 100 mM Tris (pH8.0), 0.5 mM NADH, 10 mM Pyruvate and 10 µl cell extracts. Due to the fact that pyruvate was reduced to D-lactate by NADH with D-lactate dehydrogenase, the activity of D-lactate dehydrogenase was measured by determining the absorbance reduction of NADH at 340 nm. The coefficient is 6.22 $cm^{-1}$ $mM^{-1}$. One unit of enzyme activity was defined as the amount of enzymes required for reduction of 1 µmol NADH per minute.

Results: The activity of D-lactate dehydrogenase in the metabolic evolution strain Dlac-012 was 1.5 U/mg protein, which was 1.5 times of that in recombinant *E. coli* strain Dlac-006 (1 U/mg protein).

Example 8

Construction of Recombinant *E. coli* Dlac-014

The deleted methylglyoxal synthase gene mgsA (GenBank No:ACA78263.1) was restored in recombinant *E. coli* Dlac-012 using the same methods as described in Example 1 (1-2) and resulted in a new recombinant *E. coli* strain Dlac-014. D-lac014 was deposited in CGMCC with CGMCC 7871.

The 3595 by DNA fragment I and the 1635 by DNA fragment II used for the first step and the second step homologous recombinant were amplified with primer set XZ-mgsA-up/XZ-mgsA-down by using plasmid pXZ072C and *E. coli* ATCC 8739 genome DNA as templates, respectively. The obtained recombinant *E. coli* was designed as Dlac-014. Plasmids constructed were listed in Table 3 and the primers used were listed in Table 2.

Example 9

Fermentation of Recombinant *E. coli* Dlac-014 in 500 mL Fermentation Vessel

Figure 7:
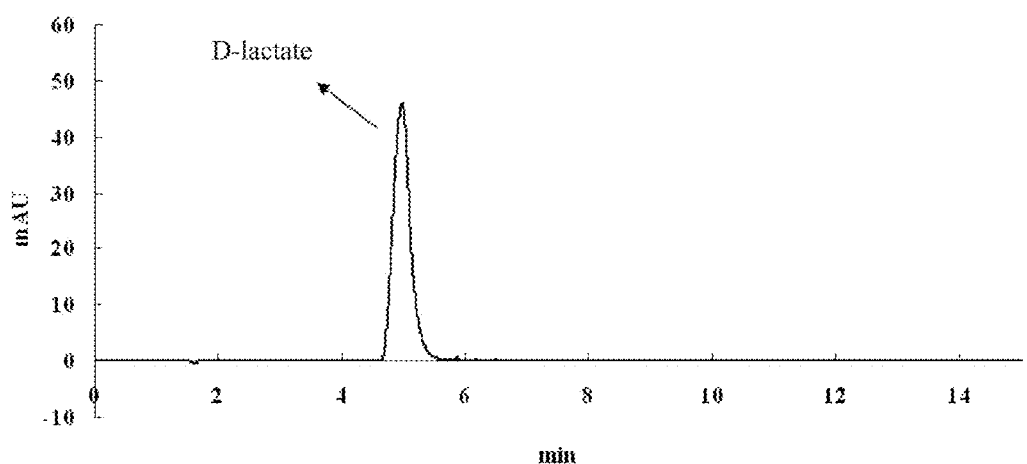
FIG. 7: the optical purity of D-lactate produced by Dlac-014 in a 500 mL fermentor.

The seed medium and fermentation medium were the same as Example 4. Results: After fermentation for 48 hours, Dlac-014 produced 800 mM D-lactate with a yield of 1.62 mol/mol (Table 4) and the optical purity of higher than 99.5% (FIG. 7).

Example 10

Construction of Recombinant *E. coli* Dlac-206

Metabolic evolution of Dlac-012 was carried out to simultaneously improve the tolerance ability to high temperature.

Fermentation medium used for metabolic evolution consisted of following components ($H_2O$ as solvent)

Major elements: glucose 120 g/L, $NH_4H_2PO_4$ 0.87 g/L, $(NH_4)_2HPO_4$ 2.63 g/L, $MgSO_4.7H_2O$ 0.18 g/L and betaine-HCl 0.15 g/L.

Trace elements: $FeCl_3.6H_2O$ 2.4 µg/L, $CoCl_2.6H_2O$ 0.3 µg/L, $CuCl_2.2H_2O$ 0.15 µg/L, $ZnCl_2$ 0.3 µg/L, $Na_2MoO_4.2H_2O$ 0.3 µg/L, $MnCl_2.4H_2O$ 0.5 µg/L, $H_3BO_3$ 0.072 µg/L.

Metabolic evolution was carried out in 500 mL fermentation vessel containing 250 mL fermentation medium. The fermentative pH was controlled at 7.0 by using 5 M ammonia as neutralizer.

For 1-190 generations, the fermentative temperature was 40° C.; Every 24 hours, the fermentation broth was transferred into a new fermentation vessel and the initial OD550 was 0.05.

For 190-360 generations, the fermentative temperature was 42° C.; Every 24 hours, the fermentation broth was transferred into a new fermentation vessel and the initial OD550 was 0.05.

Figure 8:
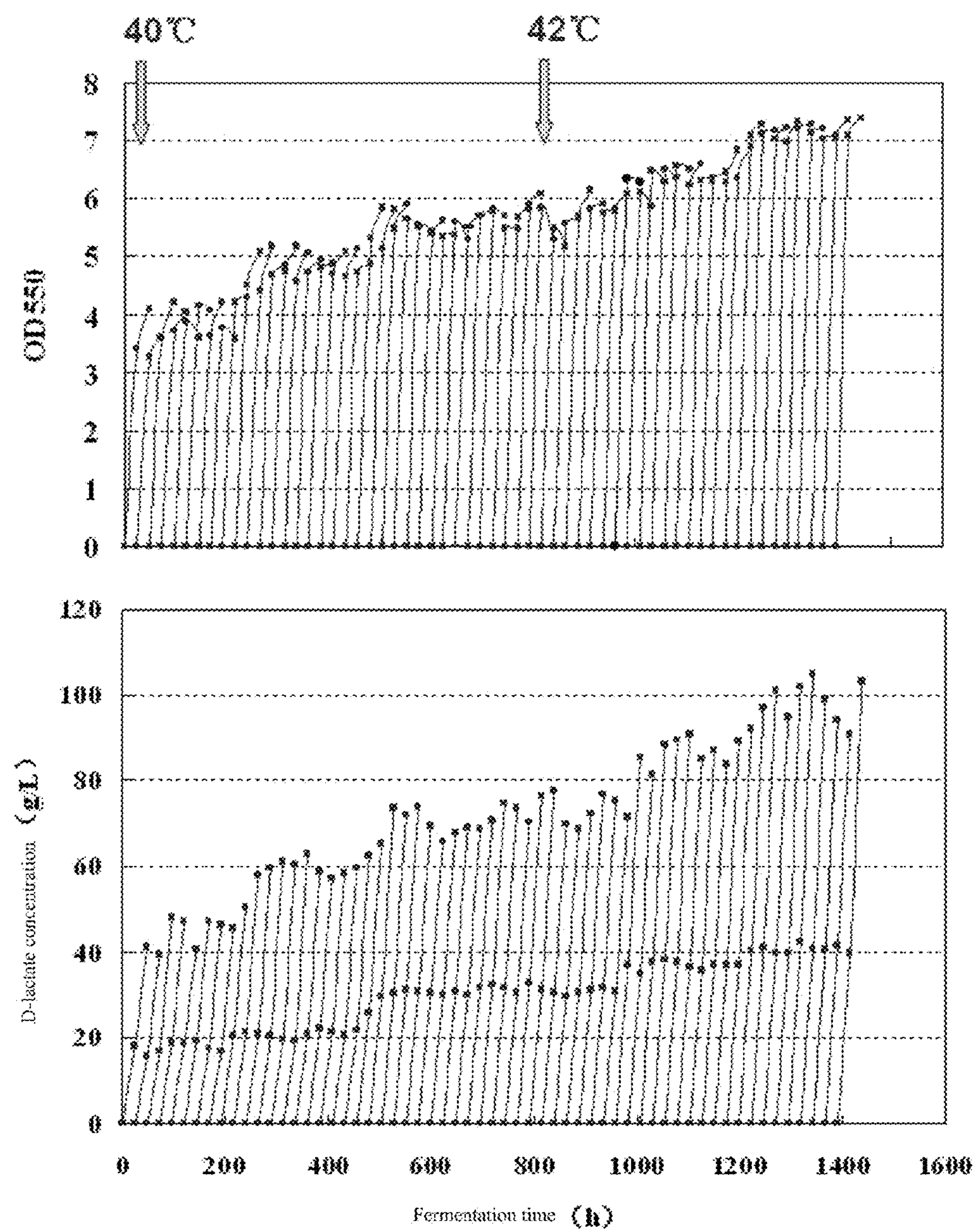
FIG. 8: the bacterial strain Dlac-206 obtained from Dlac-012 by evolution for 360 generations.

After 360 generations, a strain was obtained and named as Dlac-206 (FIG. 8). Dla-012 was deposited in CGMCC with CGMCC 7679.

Example 11

Fermentation of Recombinant *E. coli* Dlac-206 in 500 mL Fermentation Vessel The seed medium and fermentation medium were the same as Example 4.

250 mL fermentation medium was in a 500 mL fermentation vessel. 5M ammonia was used as neutralizer to control the pH at 7.0. The fermentation temperature was 42° C.

Figure 9A:
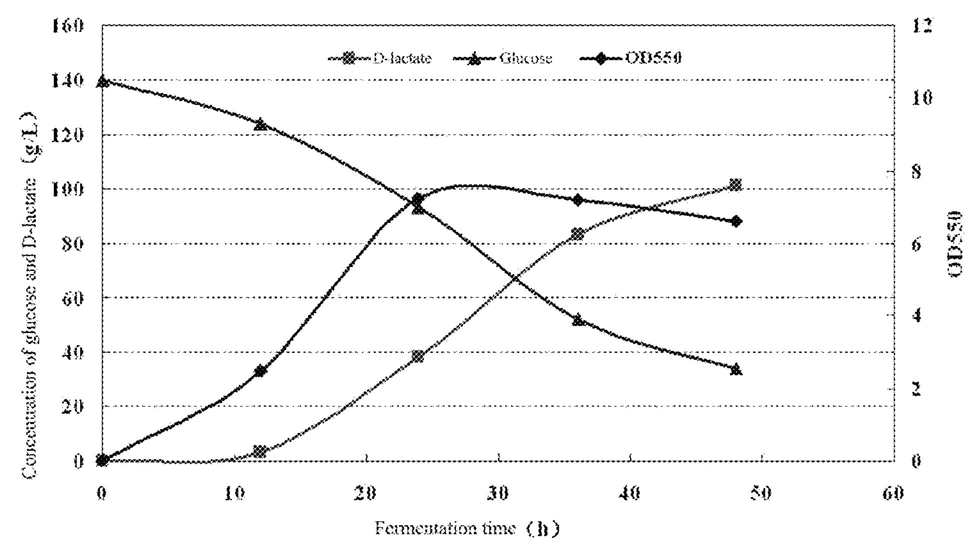
FIG. 9A shows cell growth, glucose consumption, and the production of D-lactate.
Figure 9B:
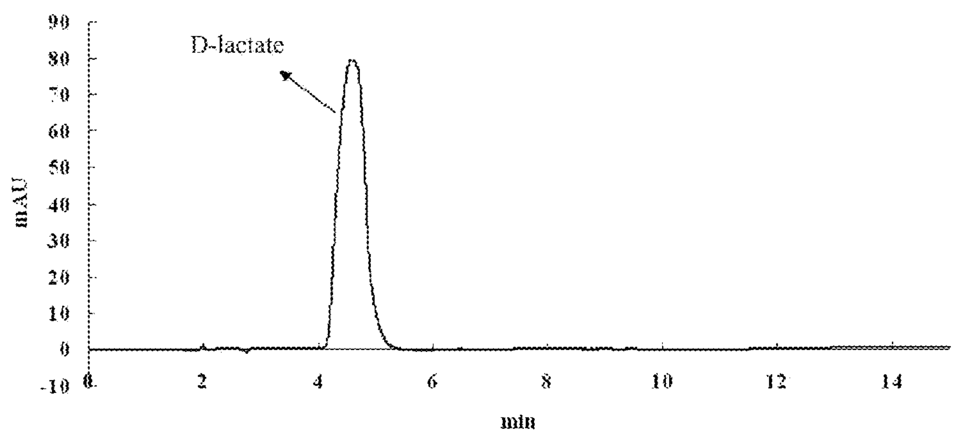
FIG. 9B shows the optical purity of D-lactate produced by fermentation.

Results were shown in FIG. 9: After fermentation for 48 hours, Dlac-206 produced 1133 mM D-lactate (102 g/L) with a yield of 1.94 mol/mol (0.97 g/g) (FIG. 9A) and the optical purity of higher than 99.5% (FIG. 9B).

Deposition Information:

The strain Dlac-012 of the invention was deposited in China General Microbiological Culture Collection Center (CGMCC) (Institute of Microbiology of Chinese Academy of Sciences, Yard 3 No. 1 Beichen West Road, Chaoyang District, Beijing) on Jun. 4, 2013 under the deposition No. CGMCC 7678, classified as *Escherichia coli.*

The strain Dlac-206 of the invention was deposited in China General Microbiological Culture Collection Center (CGMCC) (Institute of Microbiology of Chinese Academy of Sciences, Yard 3 No. 1 Beichen West Road, Chaoyang District, Beijing) on Jun. 4, 2013 under the deposition No. CGMCC 7679, classified as *Escherichia coli.*

The strain Dlac-014 of the invention was deposited in China General Microbiological Culture Collection Center (CGMCC) (Institute of Microbiology of Chinese Academy of Sciences, Yard 3 No. 1 Beichen West Road, Chaoyang District, Beijing) on Jul. 3, 2013 under the deposition No. CGMCC 7871, classified as *Escherichia coli.*

REFERENCES

Adachi E, Mikiko T, Minetaka S, Nikawa J, Shimizu K (1998) Modification of metabolic pathways of *Saccharomyces cerevisiae* by the expression of lactate dehydrogenase and deletion of pyruvate decarboxylase genes for the lactic acid fermentation at low pH value. J FermentBioengin86(3):284-289.

Bianchi M M, Brambilla L, Protani F, Liu C L, Lievense J, Porro D (2001) Efficient homolactic fermentation by *Kluyveromyces lactis* strains defective in pyruvate utilization and transformed with the heterologous LDH gene. Appl Environ Microbiol 67(12):5621-5625.

Demirici A, Pometto A (1992) Enhanced production of D(−)-lactic acid by mutants of *Lactobacillus delbrueckii* ATCC 9649. J Indust Microbiol Biotechnol 11: 23-28.

Grabar T B, Zhou S, Shanmugam K T, Yomano L P, Ingram L O (2006) Methlglyoxal bypass identified as source of chiral contamination in L(+) and D(−)-lactate fermentations by recombinant *Escherichia coli*. Biotechnol Lett 28 (19): 1527-1535.

Okano K, Zhang Q, Shinkawa S, Yoshida S, Tanaka T, Fukuda H, Kondo A (2009) Efficient production of optically pure D-lactic acid from raw corn starch by using a genetically modified L-lactate dehydrogenase gene-deficient and alpha-amylase-secreting *Lactobacillus plantarum* strain. Appl Environ Microbiol 75 (2): 462-467.

Stewart B J, Navid A, Kulp K S, Knaack J L, Bench G (2013) D-Lactate production as a function of glucose metabolism in *Saccharomyces cerevisiae*. Yeast (Chichester, England) 30(2): 81-91.

Zhou S, Causey T B, Hasona A, Shanmugam K T, Ingram L O (2003) Production of optically pure D-lactic acid in mineral salts medium by metabolically engineered *Escherichia coli* W3110. Applied Environ Microbiol 69(1): 399-407.

Zhou S, Yomano L P, Shanmugam K T, Ingram L O (2005) Fermentation of 10% (w/v) sugar to D: (−)-lactate by engineered *Escherichia coli* B. Biotechnol Lett 27 (23-24): 1891-1896.

Zhou S, Shanmugam K T, Yomano L P, Grabar T B, Ingram L O (2006) Fermentation of 12% (w/v) glucose to 1.2 M lactate by *Escherichia coli* strain SZ194 using mineral salts medium. Biotechnol Lett 28(9): 663-670.

Zhou X, Ye L Wu J (2013) Efficient production of L-lactic acid by newly isolated thermophilic *Bacillus coagulans* WCP10-4 with high glucose tolerance. Appl Microbiol Biotechnol 97(10): 4309-4314.

The invention claimed is:

1. A recombinant *E. coli*, comprising the modifications of:

inhibited expression of pflB gene, and/or inhibited activity of the protein encoded by pflB gene; and inhibited expression of frdABCD gene cluster, and/or inhibited activity of the protein(s) encoded by frdABCD gene cluster, wherein said *E. coli* further comprises a mutated ldhA gene, wherein the polypeptide encoded by the mutated ldhA gene comprises a modification at the position corresponding to position R282 in the amino acid sequence shown in SEQ ID NO: 1, wherein the modification at the position corresponding to R282 is the replacement of R with C.

2. The *E. coli* of claim 1, wherein said mutated ldhA gene further comprises a modification at the position corresponding to position C844 of the nucleotide sequence shown in SEQ ID NO: 2.

3. The *E. coli* of claim 2, wherein the modification is the replacement of C with T.

4. The *E. coli* of claim 1, wherein said mutated ldhA gene is located in a plasmid or a chromosome.

5. The *E. coli* of claim 4, wherein said *E. coli* is deposited in CGMCC under the deposition No. CGMCC 7871.

6. The *E. coli* of claim 4, wherein said *E. coli* further comprises the modifications of inhibited expression of mgsA gene, and/or inhibited activity of the protein encoded by mgsA gene.

7. The *E. coli* of claim 6, wherein said *E. coli* is the *E. coli* strain deposited in CGMCC under the deposition No. CGMCC 7678.

8. The *E. coli* of claim 6, wherein said *E. coli* is the *E. coli* strain deposited in CGMCC under the deposition No. CGMCC 7679.

9. The *E. coli* of claim 1, which is used for producing D-lactate.

10. A method for producing D-lactate, comprising:

(1) culturing the *E. coli* of claim 1 in fermentation; and (2) harvesting the produced D-lactate, optionally isolating or purifying D-lactate.

11. The method of claim 10, comprising adjusting pH by using a neutralizer in step (1), and said neutralizer is selected from ammonia or sodium hydroxide.

12. The method of claim 10, wherein the fermentation of step (1) is conducted under a high temperature, and said high temperature is 42-50° C.

* * * * *

SEQUENCE LISTING

```
<160> NUMBER OF SEQ ID NOS: 24

<210> SEQ ID NO 1
<211> LENGTH: 329
<212> TYPE: PRT
<213> ORGANISM: Escherichia coli
<220> FEATURE:
<221> NAME/KEY: PEPTIDE
<222> LOCATION: (1)..(329)

<400> SEQUENCE: 1

Met Lys Leu Ala Val Tyr Ser Thr Lys Gln Tyr Asp Lys Lys Tyr Leu
1               5                   10                  15

Gln Gln Val Asn Glu Ser Phe Gly Phe Glu Leu Glu Phe Phe Asp Phe
            20                  25                  30
```

```
Leu Leu Thr Glu Lys Thr Ala Lys Thr Ala Asn Gly Cys Glu Ala Val
        35                  40                  45

Cys Ile Phe Val Asn Asp Asp Gly Ser Arg Pro Val Leu Glu Glu Leu
    50                  55                  60

Lys Lys His Gly Val Lys Tyr Ile Ala Leu Arg Cys Ala Gly Phe Asn
65                  70                  75                  80

Asn Val Asp Leu Asp Ala Ala Lys Glu Leu Gly Leu Lys Val Val Arg
                85                  90                  95

Val Pro Ala Tyr Asp Pro Glu Ala Val Ala Glu His Ala Ile Gly Met
            100                 105                 110

Met Met Thr Leu Asn Arg Arg Ile His Arg Ala Tyr Gln Arg Thr Arg
        115                 120                 125

Asp Ala Asn Phe Ser Leu Glu Gly Leu Thr Gly Phe Thr Met Tyr Gly
    130                 135                 140

Lys Thr Ala Gly Val Ile Gly Thr Gly Lys Ile Gly Val Ala Met Leu
145                 150                 155                 160

Arg Ile Leu Lys Gly Phe Gly Met Arg Leu Leu Ala Phe Asp Pro Tyr
                165                 170                 175

Pro Ser Ala Ala Ala Leu Glu Leu Gly Val Glu Tyr Val Asp Leu Pro
            180                 185                 190

Thr Leu Phe Ser Glu Ser Asp Val Ile Ser Leu His Cys Pro Leu Thr
        195                 200                 205

Pro Glu Asn Tyr His Leu Leu Asn Glu Ala Ala Phe Glu Gln Met Lys
    210                 215                 220

Asn Gly Val Met Ile Val Asn Thr Ser Arg Gly Ala Leu Ile Asp Ser
225                 230                 235                 240

Gln Ala Ala Ile Glu Ala Leu Lys Asn Gln Lys Ile Gly Ser Leu Gly
                245                 250                 255

Met Asp Val Tyr Glu Asn Glu Arg Asp Leu Phe Phe Glu Asp Lys Ser
            260                 265                 270

Asn Asp Val Ile Gln Asp Asp Val Phe Arg Arg Leu Ser Ala Cys His
        275                 280                 285

Asn Val Leu Phe Thr Gly His Gln Ala Phe Leu Thr Ala Glu Ala Leu
    290                 295                 300

Thr Ser Ile Ser Gln Thr Thr Leu Gln Asn Leu Ser Asn Leu Glu Lys
305                 310                 315                 320

Gly Glu Thr Cys Pro Asn Glu Leu Val
                325


<210> SEQ ID NO 2
<211> LENGTH: 990
<212> TYPE: DNA
<213> ORGANISM: Escherichia coli
<220> FEATURE:
<221> NAME/KEY: gene
<222> LOCATION: (1)..(990)

<400> SEQUENCE: 2

atgaaactcg ccgtttatag cacaaaacag tacgacaaga agtacctgca acaggtgaac      60

gagtcctttg gctttgagct ggaatttttt gactttctgc tgacggaaaa aaccgctaaa     120

actgccaatg gctgcgaagc ggtatgtatt ttcgtaaacg atgacggcag ccgcccggtg     180

ctggaagagc tgaaaaagca cggcgttaaa tatatcgccc tgcgctgtgc cggtttcaat     240

aacgtcgacc ttgacgcggc aaaagaactg gggctgaaag tagtccgtgt tccagcctat     300

gatccagagg ccgttgctga acacgccatc ggtatgatga tgacgctgaa ccgccgtatt     360
```

```
caccgcgcgt atcagcgtac ccgtgacgct aacttctctc tggaaggtct gaccggcttt    420

actatgtatg gcaaaacggc aggcgttatc ggtaccggta aaatcggtgt ggcgatgctg    480

cgcattctga aaggttttgg tatgcgtctg ctggcgttcg atccgtatcc aagtgcagcg    540

gcgctggaac tcggtgtgga gtatgtcgat ctgccaaccc tgttctctga atcagacgtt    600

atctctctgc actgcccgct gacaccggaa aactaccatc tgttgaacga agccgccttc    660

gatcagatga aaaatggcgt gatgatcgtc aataccagtc gcggtgcatt gattgattct    720

caggcagcaa ttgaagcgct gaaaaatcag aaaattggtt cgttgggtat ggacgtgtat    780

gagaacgaac gcgatctgtt ctttgaagat aaatccaacg acgtgatcca ggatgacgta    840

ttccgtcgcc tgtctgcctg ccacaacgtg ctgtttaccg ggcaccaggc attcctgaca    900

gcagaagctc tgaccagtat ttctcagact acgctgcaaa acttaagcaa tctggaaaaa    960

ggcgaaacct gcccgaacga actggtttaa                                      990


<210> SEQ ID NO 3
<211> LENGTH: 329
<212> TYPE: PRT
<213> ORGANISM: Escherichia coli
<220> FEATURE:
<221> NAME/KEY: PEPTIDE
<222> LOCATION: (1)..(329)

<400> SEQUENCE: 3

Met Lys Leu Ala Val Tyr Ser Thr Lys Gln Tyr Asp Lys Lys Tyr Leu
1               5                   10                  15

Gln Gln Val Asn Glu Ser Phe Gly Phe Glu Leu Glu Phe Phe Asp Phe
            20                  25                  30

Leu Leu Thr Glu Lys Thr Ala Lys Thr Ala Asn Gly Cys Glu Ala Val
        35                  40                  45

Cys Ile Phe Val Asn Asp Asp Gly Ser Arg Pro Val Leu Glu Glu Leu
    50                  55                  60

Lys Lys His Gly Val Lys Tyr Ile Ala Leu Arg Cys Ala Gly Phe Asn
65                  70                  75                  80

Asn Val Asp Leu Asp Ala Ala Lys Glu Leu Gly Leu Lys Val Val Arg
                85                  90                  95

Val Pro Ala Tyr Asp Pro Glu Ala Val Ala Glu His Ala Ile Gly Met
            100                 105                 110

Met Met Thr Leu Asn Arg Arg Ile His Arg Ala Tyr Gln Arg Thr Arg
        115                 120                 125

Asp Ala Asn Phe Ser Leu Glu Gly Leu Thr Gly Phe Thr Met Tyr Gly
    130                 135                 140

Lys Thr Ala Gly Val Ile Gly Thr Gly Lys Ile Gly Val Ala Met Leu
145                 150                 155                 160

Arg Ile Leu Lys Gly Phe Gly Met Arg Leu Leu Ala Phe Asp Pro Tyr
                165                 170                 175

Pro Ser Ala Ala Ala Leu Glu Leu Gly Val Glu Tyr Val Asp Leu Pro
            180                 185                 190

Thr Leu Phe Ser Glu Ser Asp Val Ile Ser Leu His Cys Pro Leu Thr
        195                 200                 205

Pro Glu Asn Tyr His Leu Leu Asn Glu Ala Ala Phe Glu Gln Met Lys
    210                 215                 220

Asn Gly Val Met Ile Val Asn Thr Ser Arg Gly Ala Leu Ile Asp Ser
225                 230                 235                 240
```

```
Gln Ala Ala Ile Glu Ala Leu Lys Asn Gln Lys Ile Gly Ser Leu Gly
                245                 250                 255

Met Asp Val Tyr Glu Asn Glu Arg Asp Leu Phe Phe Glu Asp Lys Ser
            260                 265                 270

Asn Asp Val Ile Gln Asp Asp Val Phe Cys Arg Leu Ser Ala Cys His
        275                 280                 285

Asn Val Leu Phe Thr Gly His Gln Ala Phe Leu Thr Ala Glu Ala Leu
    290                 295                 300

Thr Ser Ile Ser Gln Thr Thr Leu Gln Asn Leu Ser Asn Leu Glu Lys
305                 310                 315                 320

Gly Glu Thr Cys Pro Asn Glu Leu Val
                325


<210> SEQ ID NO 4
<211> LENGTH: 990
<212> TYPE: DNA
<213> ORGANISM: Escherichia coli
<220> FEATURE:
<221> NAME/KEY: gene
<222> LOCATION: (1)..(990)

<400> SEQUENCE: 4

atgaaactcg ccgtttatag cacaaaacag tacgacaaga agtacctgca acaggtgaac      60

gagtcctttg gctttgagct ggaatttttt gactttctgc tgacggaaaa aaccgctaaa     120

actgccaatg gctgcgaagc ggtatgtatt ttcgtaaacg atgacggcag ccgcccggtg     180

ctggaagagc tgaaaaagca cggcgttaaa tatatcgccc tgcgctgtgc cggtttcaat     240

aacgtcgacc ttgacgcggc aaaagaactg ggctgaaag tagtccgtgt tccagcctat      300

gatccagagg ccgttgctga acacgccatc ggtatgatga tgacgctgaa ccgccgtatt     360

caccgcgcgt atcagcgtac ccgtgacgct aacttctctc tggaaggtct gaccggcttt     420

actatgtatg gcaaaacggc aggcgttatc ggtaccggta aaatcggtgt ggcgatgctg     480

cgcattctga aggttttgg tatgcgtctg ctggcgttcg atccgtatcc aagtgcagcg      540

gcgctggaac tcggtgtgga gtatgtcgat ctgccaaccc tgttctctga atcagacgtt     600

atctctctgc actgcccgct gacaccggaa aactaccatc tgttgaacga agccgccttc     660

gatcagatga aaaatggcgt gatgatcgtc aataccagtc gcggtgcatt gattgattct     720

caggcagcaa ttgaagcgct gaaaaatcag aaaattggtt cgttgggtat ggacgtgtat     780

gagaacgaac gcgatctgtt ctttgaagat aaatccaacg acgtgatcca ggatgacgta     840

ttctgtcgcc tgtctgcctg ccacaacgtg ctgtttaccg ggcaccaggc attcctgaca     900

gcagaagctc tgaccagtat ttctcagact acgctgcaaa acttaagcaa tctggaaaaa     960

ggcgaaacct gcccgaacga actggtttaa                                      990


<210> SEQ ID NO 5
<211> LENGTH: 30
<212> TYPE: DNA
<213> ORGANISM: Artificial
<220> FEATURE:
<223> OTHER INFORMATION: primer

<400> SEQUENCE: 5

gctaggtacc tgtgacggaa gatcacttcg                                       30


<210> SEQ ID NO 6
<211> LENGTH: 29
<212> TYPE: DNA
```

```
<213> ORGANISM: Artificial
<220> FEATURE:
<223> OTHER INFORMATION: primer

<400> SEQUENCE: 6

gctagagctc gcggctattt aacgaccct                                29


<210> SEQ ID NO 7
<211> LENGTH: 29
<212> TYPE: DNA
<213> ORGANISM: Artificial
<220> FEATURE:
<223> OTHER INFORMATION: primer

<400> SEQUENCE: 7

gctagagctc aagtaaatcg cgcgggttt                                29


<210> SEQ ID NO 8
<211> LENGTH: 33
<212> TYPE: DNA
<213> ORGANISM: Artificial
<220> FEATURE:
<223> OTHER INFORMATION: primer

<400> SEQUENCE: 8

gctaggatcc ttatttgtta actgttaatt gtc                           33


<210> SEQ ID NO 9
<211> LENGTH: 17
<212> TYPE: DNA
<213> ORGANISM: Artificial
<220> FEATURE:
<223> OTHER INFORMATION: primer

<400> SEQUENCE: 9

gtaaaacgac ggccagt                                             17


<210> SEQ ID NO 10
<211> LENGTH: 17
<212> TYPE: DNA
<213> ORGANISM: Artificial
<220> FEATURE:
<223> OTHER INFORMATION: primer

<400> SEQUENCE: 10

caggaaacag ctatgac                                             17


<210> SEQ ID NO 11
<211> LENGTH: 22
<212> TYPE: DNA
<213> ORGANISM: Artificial
<220> FEATURE:
<223> OTHER INFORMATION: primer

<400> SEQUENCE: 11

tgtccgagct taatgaaaag tt                                       22


<210> SEQ ID NO 12
<211> LENGTH: 22
<212> TYPE: DNA
<213> ORGANISM: Artificial
<220> FEATURE:
<223> OTHER INFORMATION: primer

<400> SEQUENCE: 12

cgagtaataa cgtcctgctg ct                                       22
```

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
aaacgggtaa caccccagac 20

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
cggagtgtaa acgtcgaaca 20

<210> SEQ ID NO 15
<211> LENGTH: 22
<212> TYPE: DNA
<213> ORGANISM: Artificial
<220> FEATURE:
<223> OTHER INFORMATION: primer

<400> SEQUENCE: 15
tgtgacggaa gatcacttcg ca 22

<210> SEQ ID NO 16
<211> LENGTH: 25
<212> TYPE: DNA
<213> ORGANISM: Artificial
<220> FEATURE:
<223> OTHER INFORMATION: primer

<400> SEQUENCE: 16
ttatttgtta actgttaatt gtcct 25

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
tgcagaaaac catcgacaag 20

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
caccaatcag cgtgacaact 20

<210> SEQ ID NO 19
<211> LENGTH: 20
<212> TYPE: DNA
<213> ORGANISM: Artificial
<220> FEATURE:

-continued

```
<223> OTHER INFORMATION: primer

<400> SEQUENCE: 19

gccaccatcg taatcctgtt                                                   20


<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20

atagcgcacc acctcaattt                                                   20


<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21

cagctcatca accaggtcaa                                                   20


<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22

aaaagccgtc acgttattgg                                                   20


<210> SEQ ID NO 23
<211> LENGTH: 20
<212> TYPE: DNA
<213> ORGANISM: Artificial
<220> FEATURE:
<223> OTHER INFORMATION: primer

<400> SEQUENCE: 23

agcgttatct cgcggaccgt                                                   20


<210> SEQ ID NO 24
<211> LENGTH: 20
<212> TYPE: DNA
<213> ORGANISM: Artificial
<220> FEATURE:
<223> OTHER INFORMATION: primer

<400> SEQUENCE: 24

aagtgcgagt cgtcagttcc                                                   20
```